US010173024B2

(12) United States Patent
Kooij et al.

(10) Patent No.: US 10,173,024 B2
(45) Date of Patent: Jan. 8, 2019

(54) FLEXIBLE FOREHEAD SUPPORT

(71) Applicant: ResMed Limited, Bella Vista, New South Wales (AU)

(72) Inventors: Michiel Kooij, Amsterdam (NL); Dimitri Marco Maurer, Gosford (AU)

(73) Assignee: ResMed Limited, Bella Vista (AU)

( * ) Notice: Subject to any disclaimer, the term of this patent is extended or adjusted under 35 U.S.C. 154(b) by 0 days.

(21) Appl. No.: 14/220,633

(22) Filed: Mar. 20, 2014

(65) Prior Publication Data

US 2014/0202465 A1    Jul. 24, 2014

Related U.S. Application Data

(63) Continuation of application No. 12/213,536, filed on Jun. 20, 2008, now Pat. No. 8,720,443.

(30) Foreign Application Priority Data

Jun. 22, 2007    (AU) ................ 2007903360

(51) Int. Cl.
*A61M 16/06* (2006.01)
*A61M 16/08* (2006.01)

(52) U.S. Cl.
CPC ........ *A61M 16/0644* (2014.02); *A61M 16/06* (2013.01); *A61M 16/0622* (2014.02); *A61M 16/0633* (2014.02); *A61M 16/0825* (2014.02); *A61M 16/0605* (2014.02); *A61M 2205/0216* (2013.01)

(58) Field of Classification Search
CPC ............. A61M 16/06; A61M 16/0605; A61M 16/0622; A61M 16/0633; A61M 16/0644; A61M 16/065; A61M 16/0661

USPC ........... 128/203.29, 204.11, 205.25, 206.21, 128/206.24–206.25, 206.28, 207.11, 128/207.13, 207.17

See application file for complete search history.

(56) References Cited

U.S. PATENT DOCUMENTS

| | | | |
|---|---|---|---|
| 5,517,986 A | 5/1996 | Starr et al. | |
| 6,196,223 B1* | 3/2001 | Belfer | A41D 13/1176 128/205.25 |
| 6,347,631 B1 | 2/2002 | Hansen et al. | |
| 6,427,694 B1* | 8/2002 | Hecker | A61M 16/06 128/201.22 |

(Continued)

FOREIGN PATENT DOCUMENTS

| | | |
|---|---|---|
| DE | 10 2005 033 648 | 1/2007 |
| EP | 1555039 | 7/2005 |

(Continued)

OTHER PUBLICATIONS 5 photographs of Hoffrichter Silicone CPAP Nasal Mask, USPTO to assume before Applicant's filing date.

(Continued)

*Primary Examiner* — Gregory Anderson
*Assistant Examiner* — Victoria Murphy
(74) *Attorney, Agent, or Firm* — Nixon & Vanderhye P.C.

(57) ABSTRACT

A respiratory mask includes a mask frame and a forehead support provided to the mask frame. The forehead support includes a base extending from the frame. The base includes a flexible portion along at least a portion of its length including a material and/or physical characteristic that allows the base to flex from an original, unloaded position.

29 Claims, 40 Drawing Sheets

(56) References Cited

U.S. PATENT DOCUMENTS

| | | | | |
|---|---|---|---|---|
| 6,520,182 | B1* | 2/2003 | Gunaratnam | A61M 16/06 128/206.27 |
| 6,532,961 | B1 | 3/2003 | Kwok et al. | |
| 6,860,269 | B2 | 3/2005 | Kwok et al. | |
| 7,044,130 | B2 | 5/2006 | Jones et al. | |
| 7,047,971 | B2 | 5/2006 | Ho et al. | |
| 7,069,932 | B2 | 7/2006 | Eaton et al. | |
| 7,156,096 | B2* | 1/2007 | Landis | 128/204.18 |
| 7,216,647 | B2 | 5/2007 | Lang et al. | |
| 7,357,136 | B2 | 4/2008 | Ho et al. | |
| 7,819,119 | B2* | 10/2010 | Ho | 128/206.24 |
| 8,720,443 | B2* | 5/2014 | Kooij et al. | 128/207.11 |
| 8,789,532 | B2* | 7/2014 | Hansen | A61M 16/06 128/206.21 |
| 2002/0023649 | A1* | 2/2002 | Gunaratnam | A61M 16/06 128/205.25 |
| 2004/0035427 | A1 | 2/2004 | Bordewick et al. | |
| 2004/0216747 | A1 | 11/2004 | Jones, Jr. et al. | |
| 2004/0255950 | A1 | 12/2004 | Gradon et al. | |
| 2005/0022820 | A1 | 2/2005 | Kwok et al. | |
| 2005/0072428 | A1 | 4/2005 | Ho et al. | |
| 2005/0076913 | A1 | 4/2005 | Ho et al. | |
| 2005/0155603 | A1 | 7/2005 | Frerichs et al. | |
| 2006/0076019 | A1* | 4/2006 | Ho | 128/206.24 |
| 2006/0283462 | A1 | 12/2006 | Woodard et al. | |
| 2007/0221226 | A1* | 9/2007 | Hansen | A61M 16/06 128/206.21 |
| 2008/0314388 | A1 | 12/2008 | Brambilla et al. | |
| 2010/0071700 | A2 | 3/2010 | Hitchcock et al. | |

FOREIGN PATENT DOCUMENTS

| | | |
|---|---|---|
| NZ | 551715 | 2/2011 |
| WO | WO 2001/32250 | 5/2001 |
| WO | WO 2004/078229 | 9/2004 |
| WO | WO 2005/123166 | 12/2005 |
| WO | WO 2006/000046 | 1/2006 |

OTHER PUBLICATIONS

European Search Report issued in European Application No. 08158708.2 (dated Jan. 30, 2009).
Examination Report dated Jun. 23, 2008 in New Zealand Application No. 569226.
Examination Report issued in New Zealand Application No. 581726 (dated Mar. 1, 2011).
Examination Report issued in New Zealand Application No. 591096 (dated Feb. 15, 2011).
First Examination Report issued in a corresponding New Zealand Application No. 617380 dated Nov. 12, 2013.
Examination Report issued in a related New Zealand Application No. 599979, dated May 16, 2012.
Examiner's email of Jul. 25, 2012 to New Zealand associate regarding incorrect number on first citation in the Examination Report dated May 16, 2012 for New Zealand Application No. 599979.
Further Examination Report issued in corresponding New Zealand Appln. No. 617380, dated Mar. 4, 2015.
First Examination Report issued in corresponding New Zealand Application No. 706184 dated May 20, 2015.
Extended European Search Report issued in corresponding European Application No. 10 19 6180.3 dated Sep. 21, 2015.
Further Examination Report issued in corresponding New Zealand Application No. 706184 dated May 10, 2016.
Office Action dated Feb. 8, 2017 issued in European Application No. 10196180.3 (7 pages).
Extended Search Report dated Nov. 14, 2016 issued in European Application No. 10196186.0 (8 pages).
First Examination Report dated Dec. 14, 2016 issued in New Zealand Application No. 726206 (3 pages).
Further Examination Report dated May 23, 2018 issued in New Zealand Application No. 726206 (3 pages).
First Examination Report dated May 23, 2018 issued in New Zealand Application No. 741939 (2 pages).
Communication dated Apr. 17, 2018 issued in European Application No. 10196186.0 (5 pages).

* cited by examiner

Fig. 17-1
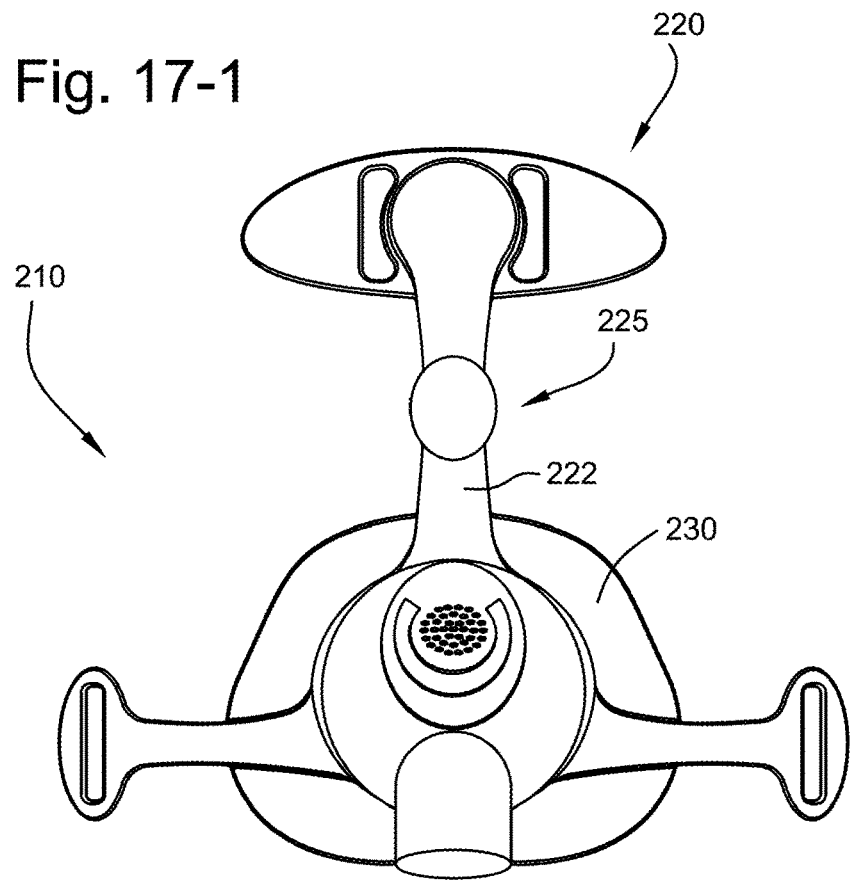
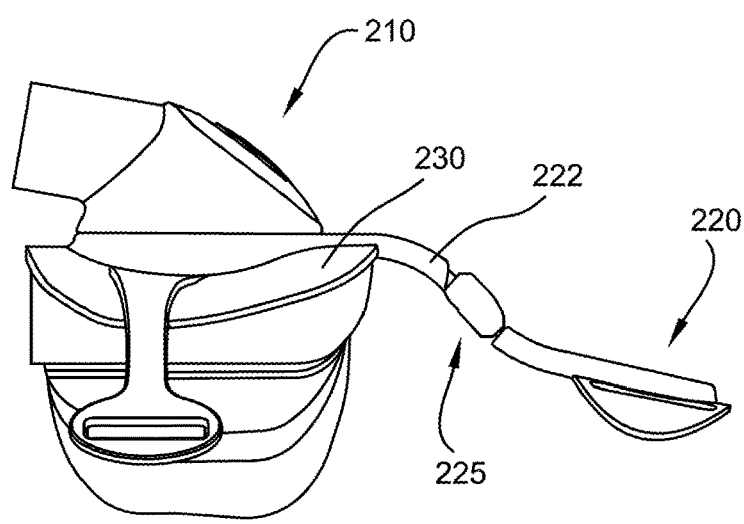
Fig. 17-2

FLEXIBLE FOREHEAD SUPPORT

CROSS-REFERENCE TO APPLICATION

This application is a continuation of U.S. patent application Ser. No. 12/213,536, filed Jun. 20, 2008, now U.S. Pat. No. 8,720,443, which claims the benefit of Australian Provisional Application No. AU 2007903360, filed Jun. 22, 2007, each of which is incorporated herein by reference in its entirety.

FIELD OF THE INVENTION

The present invention relates to a respiratory mask, and more particularly, to a forehead support for a respiratory mask.

BACKGROUND OF THE INVENTION

FIG. 1 illustrates a respiratory mask produced by ResMed including a forehead support (e.g., see U.S. Pat. No. 6,532,961). The ResMed forehead support has two primary functions. The first primary function is to stabilize the cushion on the patient's face to facilitate a seal. The forehead support mainly acts to prevent axial rotation about the horizontal and median axes as shown in FIG. 1.

The second primary function is to correctly locate the cushion against the patient's facial profile, again facilitating the generation of a seal. In prior forehead supports produced by ResMed, the two variables controlled by the forehead support are the displacement of the cushion (depicted by X in FIG. 2a) in the horizontal plane and also the angle (depicted by θ in FIG. 2a) of the cushion's sealing surface to the frontal plane. FIGS. 2a to 2c illustrate alternative positions of the forehead support to vary the displacement and angle of the cushion. By allowing variations in the displacement and angle of the cushion, a compromise between generation of a seal and prevention of excessive force on sensitive areas, such as the nasal bridge, can be achieved, thus maximizing patient comfort.

Adjustment of the displacement and angle can also be used to maximize the contact area between the forehead support and the patient's forehead. By maximizing the contact area, the overall force on the patient's forehead may be reduced, which improves patient comfort.

SUMMARY OF THE INVENTION

A first aspect of the present invention relates to the provision of a flexible and/or resilient forehead support for a respiratory mask.

One advantage of embodiments of the invention is that the forehead support is auto-fitting. This is beneficial because it overcomes the problems arising from the fact that some patients do not realize that the forehead support is adjustable, do not adjust it correctly, and/or have difficulty adjusting it while wearing the mask because of dexterity and/or the lack of line of sight (i.e., you cannot easily see something that is between your eyes).

Another advantage of embodiments of the invention is that, as compared to a typical adjustable forehead support, at least one if not more components can be eliminated from the design. This is beneficial in that: (1) design complexity is reduced leading to cost savings in the design process, (2) at least one part is removed providing a reduction in the cost of goods, and (3) there are less assembly steps resulting in a reduction in assembly time and associated cost savings. It is also simpler for patients as there is no intricate reassembly of the forehead support required after cleaning.

A second aspect of the present invention relates to the provision of an adjustable forehead support using one or more resilient elements that may or may not be integrated with one or more rigid or semi-rigid elements. If more than one resilient element is provided, each element could have a different spring constant. The resilient elements may be joined to the rigid or semi-rigid elements by over-molding, adhesive, or other suitable manufacturing technique.

In this specification, the word "resilient" is used to describe any material that under normal usage conditions in this context exhibits a range of elastic deformation in response to a force applied to the material that is sufficient to allow the forehead support to flex across a useful angular range in any plane or to extend or compress axially.

A third aspect of the present invention relates to the provision of an adjustable forehead support comprising one or more regions of reduced cross-sectional area or reduced outer cross-sectional footprint that are resilient. These regions may take the form of substantially superposed recesses or an array of recesses that are disposed around at least a portion of an outer surface of the forehead support. These recesses may be disposed transversely to the main axis of the mask. In one embodiment, these recesses are disposed perpendicularly to the main axis of the mask.

In one variation of the third aspect, one or more layers of more resilient or flexible material may be provided adjacent each region of reduced cross-sectional area or reduced outer cross-sectional footprint. Each layer may provide a spring or dampening function and may be joined to each region by over-molding, adhesive or another suitable manufacturing technique.

One advantage of some embodiments of this invention is a controlled amount of torsional flexation or resilience can be provided. This can be beneficial to patients who have an asymmetric facial profile or to patients who do not have their mask located correctly on their face.

Another aspect of the present invention is the provision of a respiratory mask having a forehead support of any one of the embodiments of the present invention.

Another aspect of the present invention is the provision of a respiratory mask system having a forehead support of any one of the embodiments of the present invention.

Another aspect of the present invention is a method of fitting a respiratory mask to a patient comprising: (1) locating the cushion on the patient's face, (2) placing the headgear straps around the patient's head; and (3) allowing the forehead support to automatically attain a customized orientation.

Another aspect of the present invention relates to a respiratory mask including a mask frame and a forehead support provided to the mask frame. The forehead support includes a base extending from the frame. The base includes a flexible portion along at least a portion of its length including a material and/or physical characteristic that allows the base to flex from an original, unloaded position.

Another aspect of the present invention relates to a respiratory mask including a mask frame and a forehead support provided to the mask frame. The forehead support includes a base extending from the frame. The base includes a flexible portion along at least a portion of its length which allows the base to flex from an original, unloaded position. The flexible portion is constructed of a different material than the remainder of the base.

Another aspect of the present invention relates to a respiratory mask including a mask frame and a forehead support provided to the mask frame. The forehead support includes a base extending from the frame. The base includes a bendable portion along at least a portion of its length which allows the base to bend from an original position to an adjusted position such that the bendable portion retains the adjusted position for forces less than a certain limit. The bendable portion includes a deformable or malleable material.

Another aspect of the present invention relates to a respiratory mask including a mask frame adapted to support an elbow and a forehead support integrally formed in one piece with the mask frame. The forehead support includes a general "T"-shape with a base extending from the frame and an upper cross-portion provided to the base. The base includes a flexible portion along at least a portion of its length that is constructed of a resilient material that allows the base to flex from an original, unloaded position and substantially return to its original position when not loaded.

Another aspect of the present invention relates to a respiratory mask including a mask frame and a forehead support provided to the mask frame. The forehead support includes a base extending from the frame. The base includes a flexible portion along at least a portion of its length that allows the forehead support to flex across a useful angular range in any plane and/or to extend or compress axially.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 3-1 to 3-7 are various views of a respiratory mask including a forehead support according to an embodiment of the present invention;

FIGS. 4-1 to 4-8 are various views of a frame of the mask shown in FIGS. 3-1 to 3-7;

FIG. 5 is a side view of the mask shown in FIGS. 3-1 to 3-7 showing flexing in opposing directions according to an embodiment of the present invention;

FIG. 6 is a side view of the mask shown in FIGS. 3-1 to 3-7 showing a range of movement of the forehead support according to an embodiment of the present invention;

FIGS. 7-1 and 7-2 are side views of the mask shown in FIGS. 3-1 to 3-7 showing an orientation of the forehead support according to an embodiment of the present invention;

FIGS. 8-1 and 8-2 are side views of the mask shown in FIGS. 3-1 to 3-7 showing an orientation of the forehead support according to another embodiment of the present invention;

FIGS. 15-1 to 15-8 are various views of an elbow of the mask shown in FIGS. 3-1 to 3-7;

FIG. 15-9 is a cross-sectional view illustrating attachment of the elbow to the frame according to an embodiment of the present invention;

FIGS. 16-1 to 16-4 are various views of a swivel joint of the mask shown in FIGS. 3-1 to 3-7;

FIGS. 17-1 to 17-2 are front and side views of a mask including a forehead support with different materials according to an embodiment of the present invention;

FIGS. 17-3 to 17-4 are side views of the mask shown in FIGS. 17-1 to 17-2 with the forehead support in first and second deformed positions;

FIGS. 20-1 and 20-2 are side views of a mask including a forehead support according to another embodiment of the present invention.

DETAILED DESCRIPTION OF ILLUSTRATED EMBODIMENTS

Figure 1:
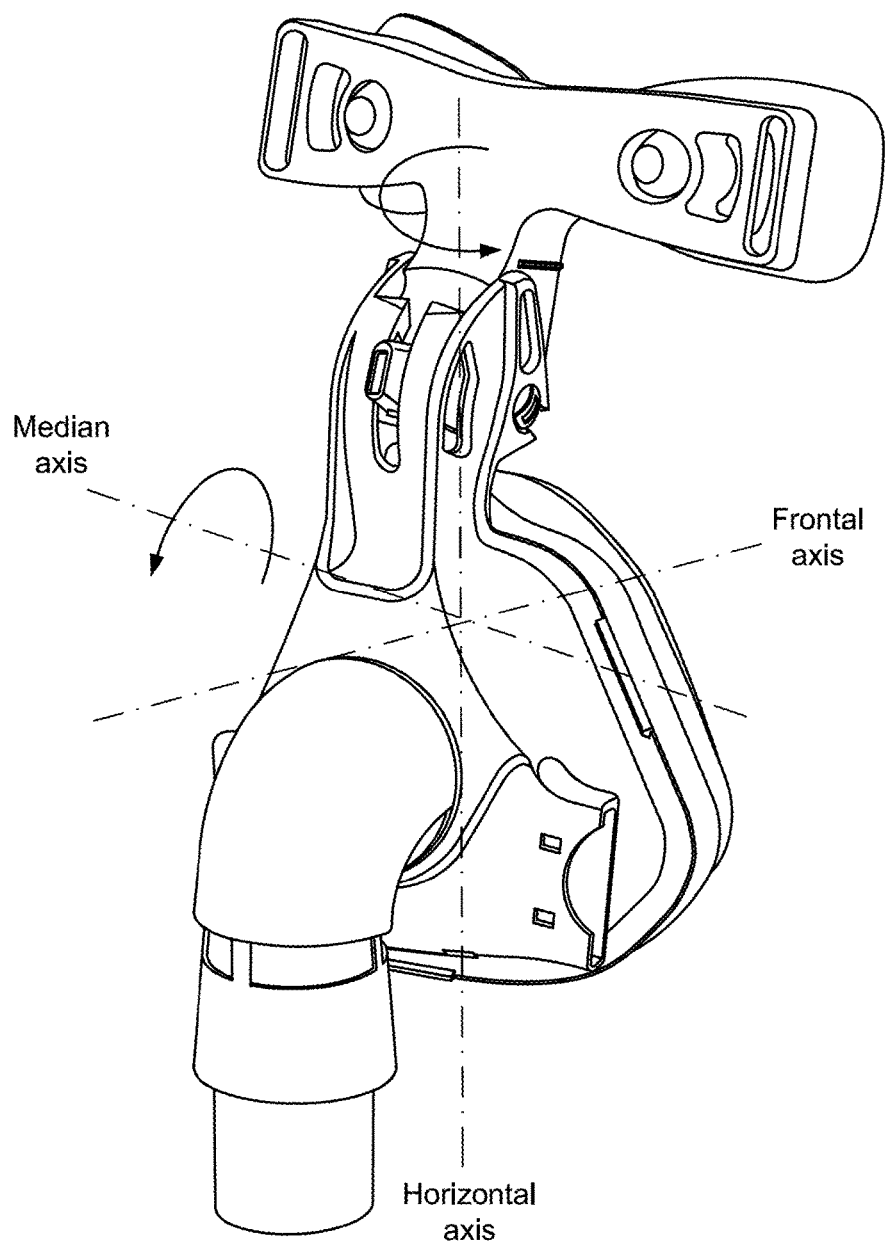
FIG. 1 is a front perspective view of a prior art mask including a forehead support.
Figure 2A:
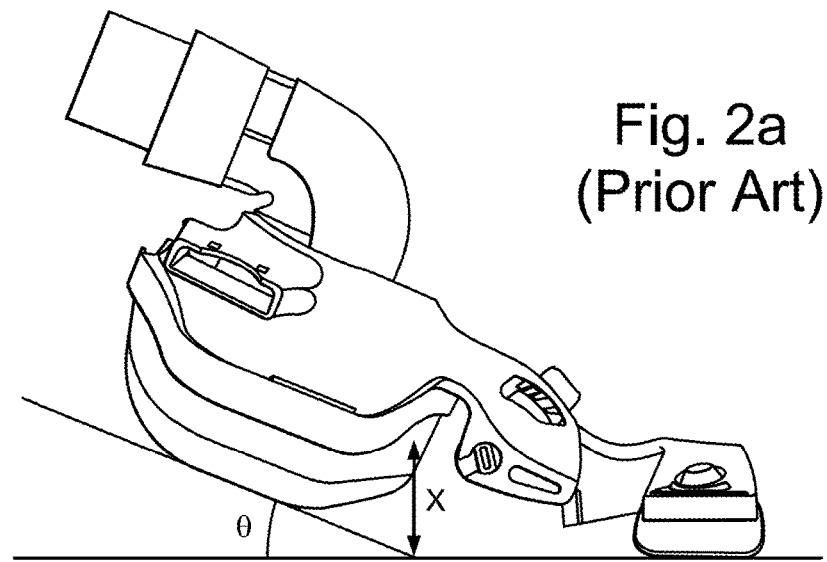
FIGS. 2a to 2c are side views of the prior art mask of FIG. 1 showing various positions of the forehead support.
Figure 2B:
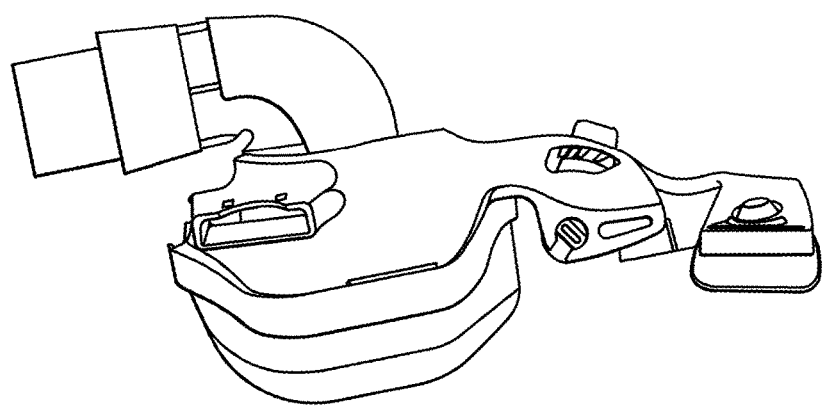
Figure 2C:
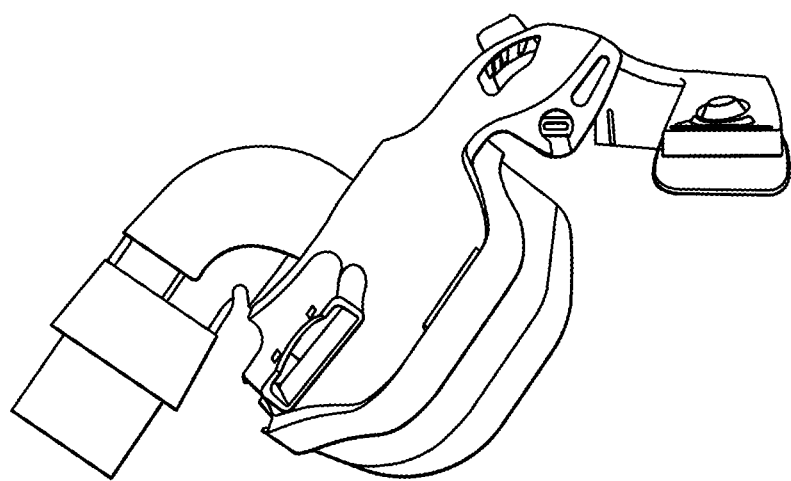

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

1. First Embodiment of Forehead Support

FIGS. 3-1 to 3-7 illustrates a respiratory mask 10 including a forehead support 20 according to an embodiment of the present invention. In this embodiment, the mask 10 includes a nasal interface. As illustrated, the mask 10 includes a frame 30, a cushion 40 provided to the frame 30 and adapted to form a seal with the patient's face, an elbow 50 provided to the frame 30 and adapted to be connected to an air delivery tube that delivers breathable gas to the patient, and a forehead support 20 to provide a support and stability mechanism between the mask 10 and the patient's forehead.

A headgear assembly (not shown) may be removably attached to the frame 30 and the forehead support 20 to maintain the mask 10 in a desired adjusted position on the patient's face. The mask 10 is intended for use in positive pressure therapy for users with obstructive sleep apnea (OSA) or another respiratory disorder.

While the forehead support 20 is described as being implemented into a nasal mask, it may be adapted for use with other suitable interface types. That is, the interface type is merely exemplary, and each embodiment may be adapted to include other interface types, e.g., full face interface, nasal pillows, prongs, etc.

1.1 Frame/Forehead Support

In the illustrated embodiment, the frame 30 and forehead support 20 are integrally formed as a one-piece structure. For example, the frame 30 and forehead support 20 may be a single part manufactured from a single material.

As shown in FIGS. 4-1 to 4-8, the frame 30 includes inner and outer walls that define an annular channel 32 structured to retain the cushion 40. The cushion 40 may include various configurations, e.g., dual wall, gusseted, and/or cushions similar to ResMed's Mirage Vista™ mask or ResMed's Mirage Micro™ mask, etc.

The frame 30 also includes a tube portion 34 structured to retain the elbow 50, as described in greater detail below.

In addition, headgear connectors 36 are provided to respective sides of the frame 30. Each headgear connector 36 is in the form of an outrigger including an elongated arm 36(1) and a tab portion 36(2) that provides a slot 36(3) adapted to receive a respective headgear strap in use (e.g., see FIGS. 3-1 and 4-1). In an embodiment, each slot 36(3) may be open-ended (e.g., see FIG. 14).

The forehead support 20 extends from a top of the frame 30. The forehead support 20 has a general "T"-shape, with a base 22 and an upper cross portion 24. The upper cross portion 24 provides a pair of arms 24(1), and each arm 24(1) includes a slot 24(2) adapted to receive a respective headgear strap (e.g., see FIGS. 3-1 and 4-3). In an embodiment, each slot 24(2) may be open-ended.

In addition, the upper cross-portion 24 may be structured to retain one or more forehead pads (e.g., elastomeric, gel, or foam pad). In an alternative embodiment, a headgear strap from the headgear may be used as forehead padding as described in Australian Provisional Application No. AU 2007903361, filed Jun. 22, 2007, entitled "Forehead Support for a Facial Mask", which is incorporated herein by reference in its entirety.

As described in greater detail below, the base 22 of the forehead support 20 is contoured along its length and includes a flexible and/or resilient portion 25 along at least a portion of the base's length which allows the forehead support to flex across a useful angular range in any plane and/or to extend or compress axially in use. In an embodiment, the base 22 provides a low profile (e.g., see FIGS. 3-7 and 4-8) that is contoured to substantially match the curvature of the patient's face with minor adjustment provided by the flexible portion 25 of the base 22. In an embodiment, the entire length of the base and/or upper cross portion may be bendable to intimately follow the facial contours of the patient's face.

Such arrangement provides the forehead support 20 with a range of adjustment and allows the forehead support to be auto-fitting wherein the forehead support may automatically attain a customized orientation. That is, the forehead support 20 does not include an adjustment mechanism per se that needs to be manually adjusted by the patient in order to fit the mask to the patient's face.

In addition, the flexible forehead support 20 may provide a force to seal the cushion 40 over the patient's nasal bridge. In an embodiment, the magnitude of forces to flex the forehead support may be similar to the magnitude of forces to deform the mask seal or cushion (e.g., forces are balanced), which helps to ensure a seal when the forehead support is sufficiently tightened into position. In an embodiment, the forehead support may be structured to redistribute forces on the cushion.

The base 22 of the forehead support 20 extends along the dead space in the patient's field of view (between the eyes) so it is not substantially in the patient's field of view in use, i.e., unobtrusive and eliminates interference with bedding material. Optimally, the forehead support 20 is not visible at all by the patient in use.

It should be appreciated that the illustrated forehead support 20 is exemplary and other suitable arrangements are possible. For example, the upper cross portion 24 may be shorter or longer in length, may include tapered ends to reduce material, and/or may be wider to increase surface area of contact. Many different geometries of the upper cross portion 24 may be adopted in order to provide a relatively large surface area and hence low contact pressure and to improve lateral stability of the mask in use. In an embodiment, the forehead support 20 may merely include the base 22 with an end that provides spaced-apart openings for looping respective headgear straps (e.g., I-beam construction).

1.2 Flexibility

Figures 1, 3:
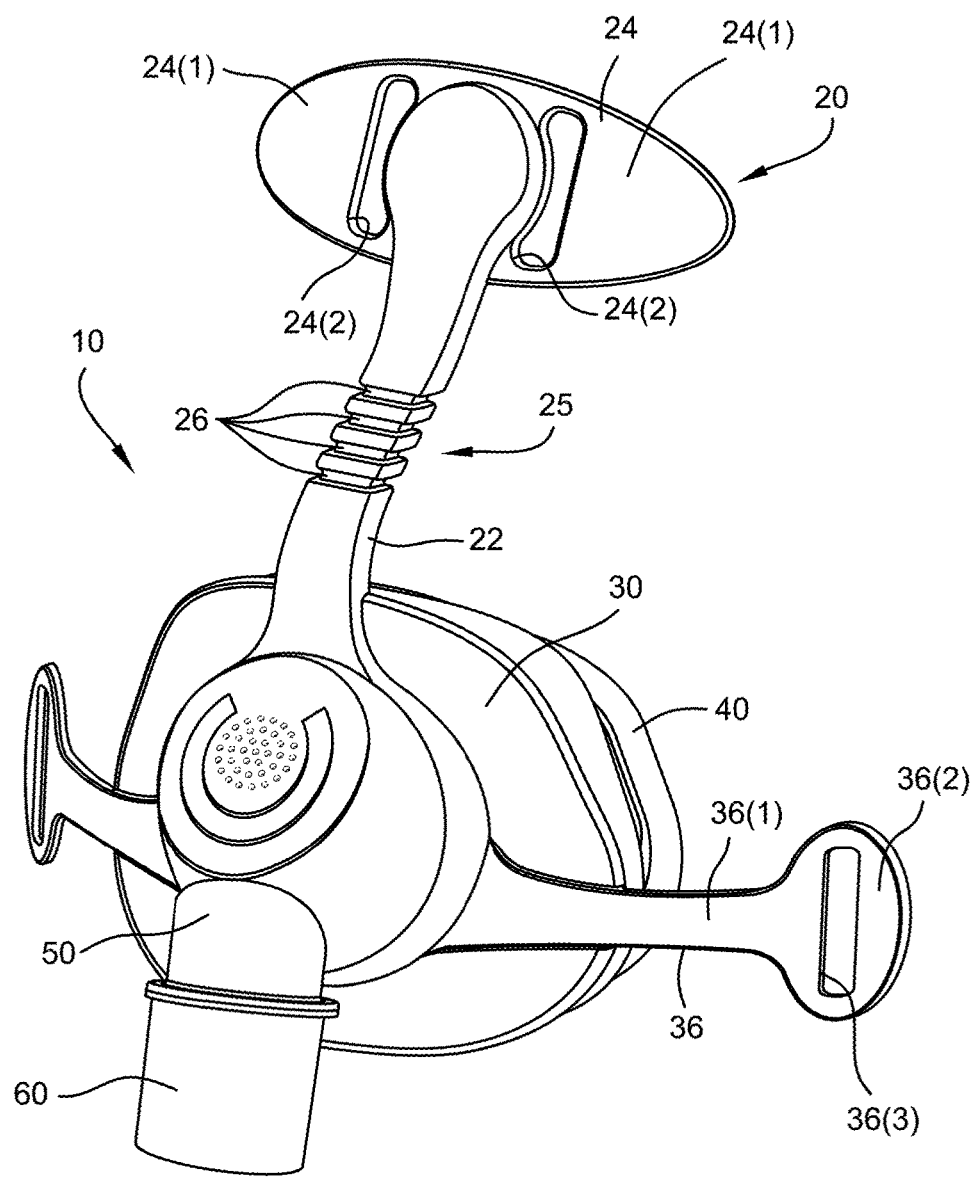
Figures 2, 3:
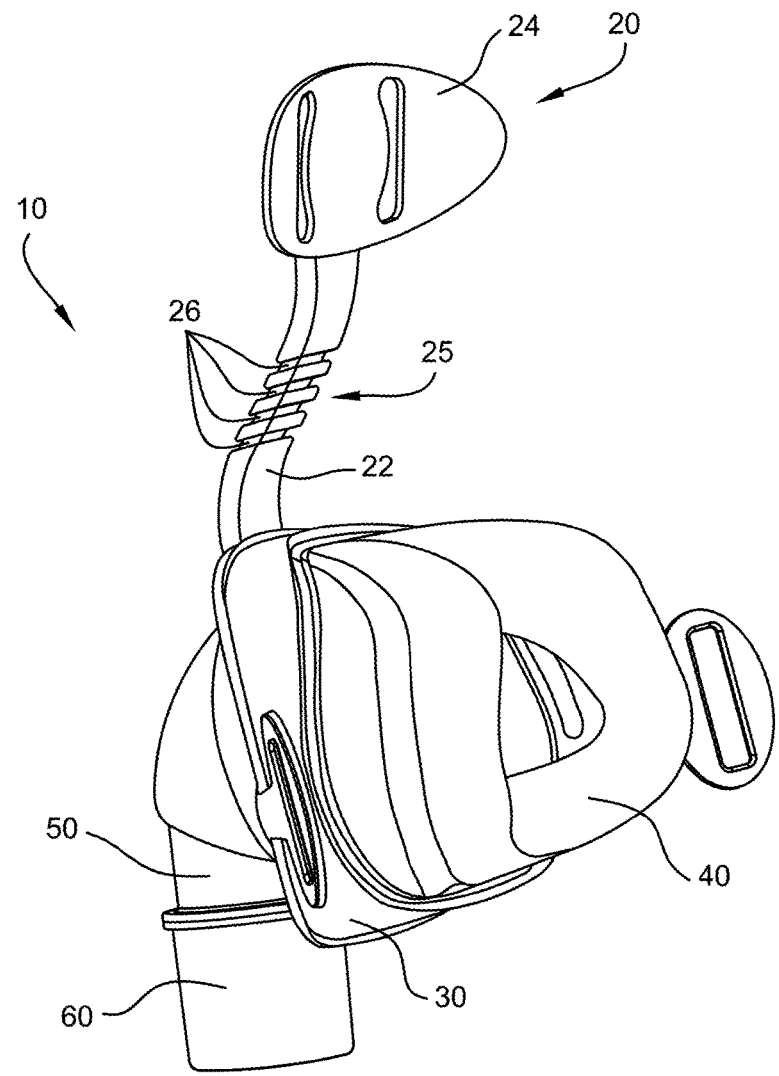
Figure 3:
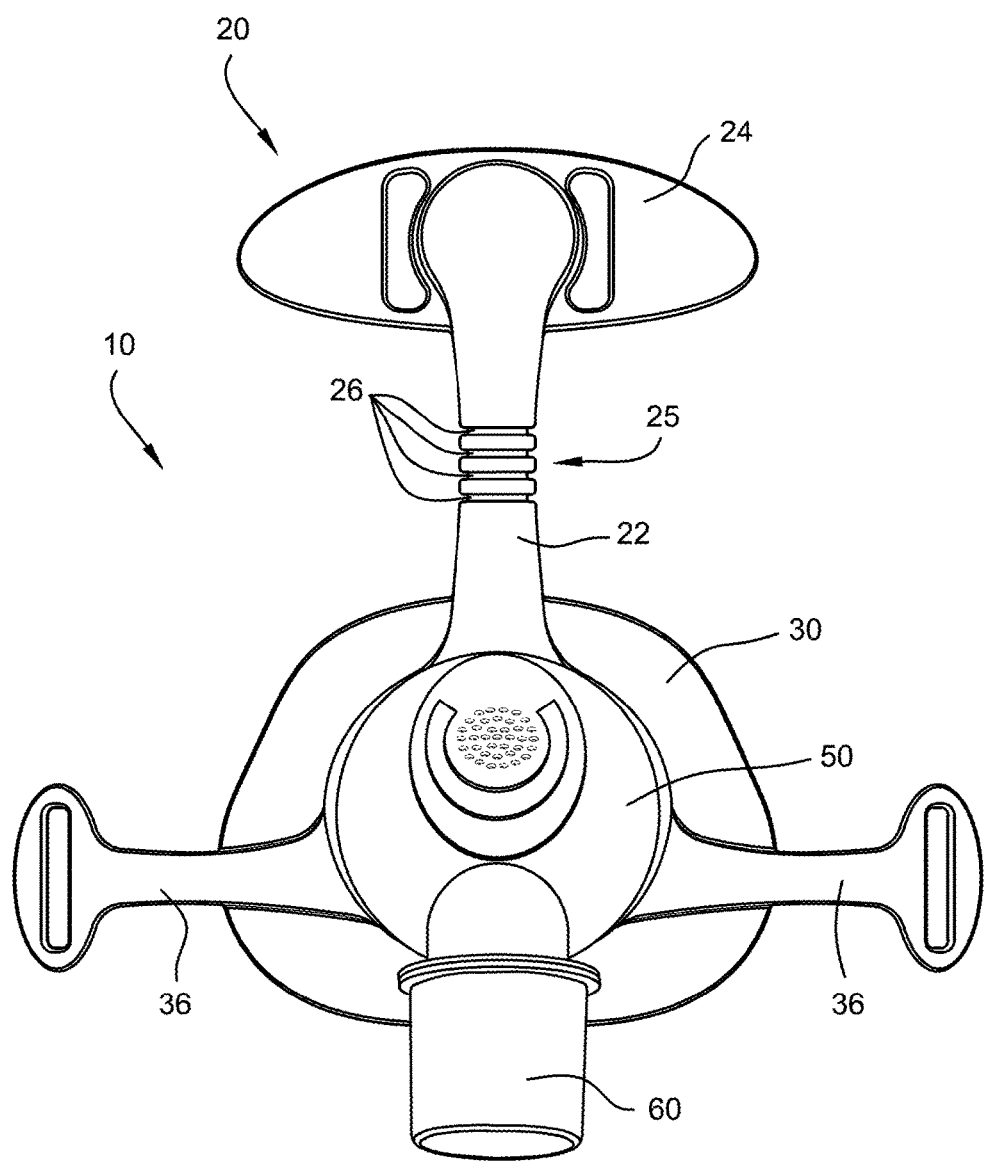
Figures 3, 4:
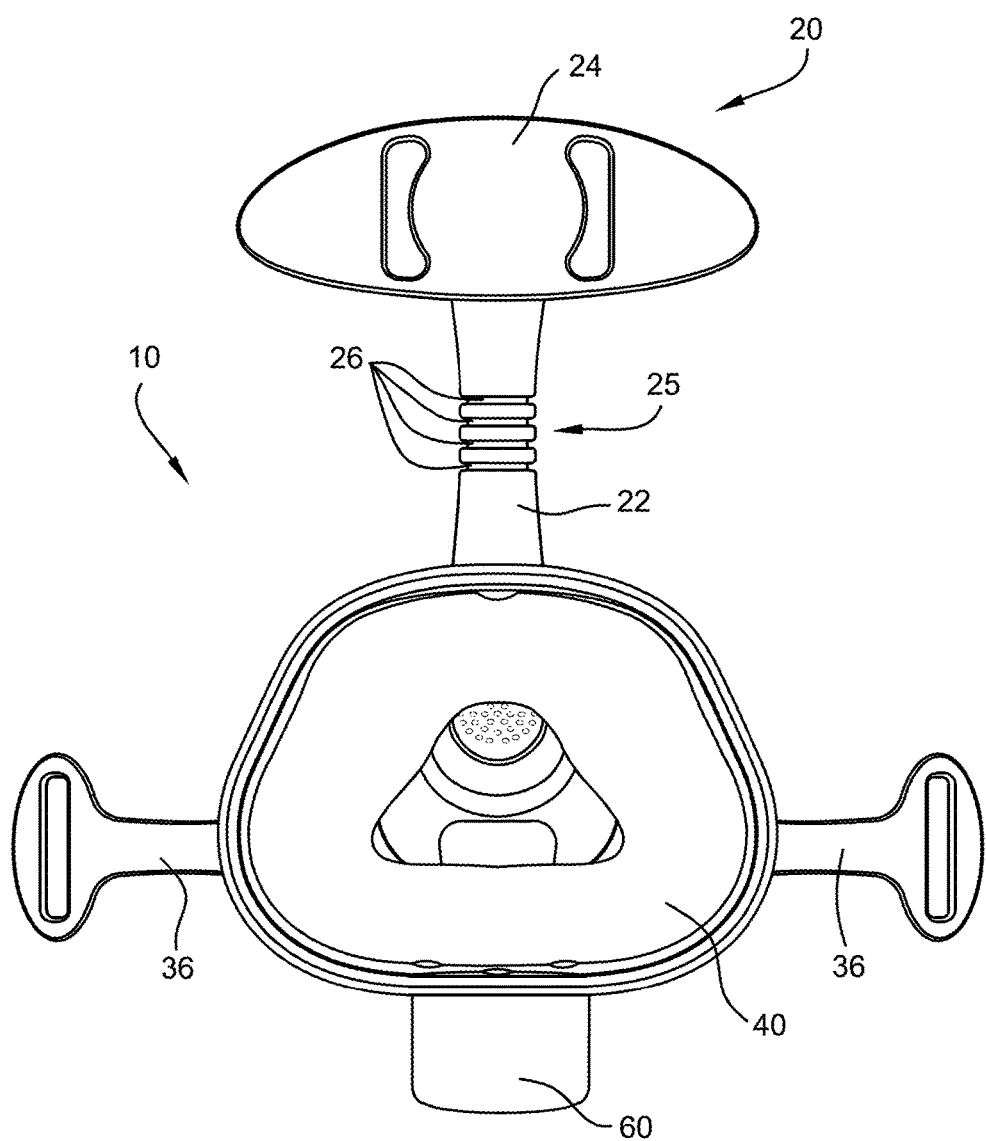
Figures 3, 4, 5:
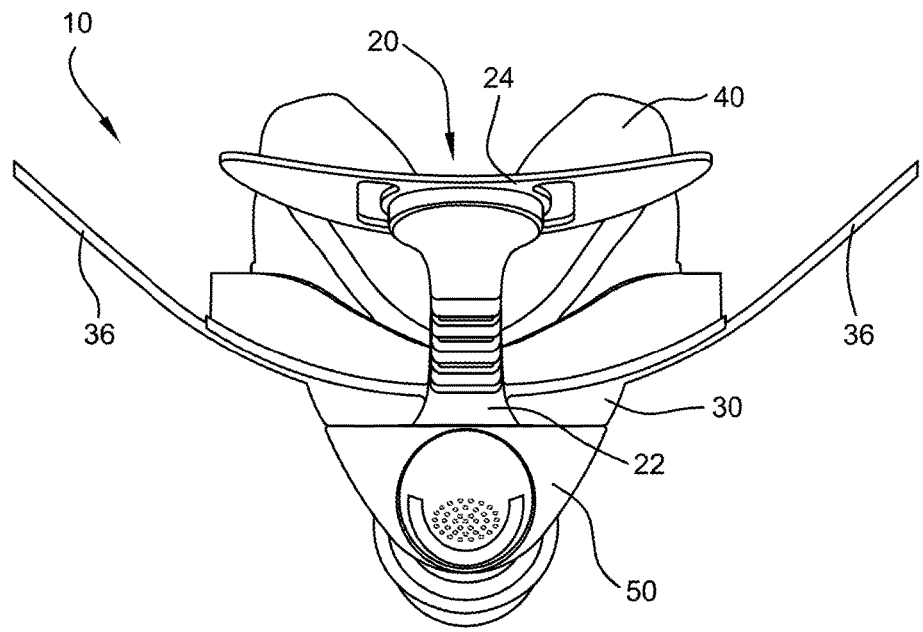
Figures 3, 4, 5, 6:
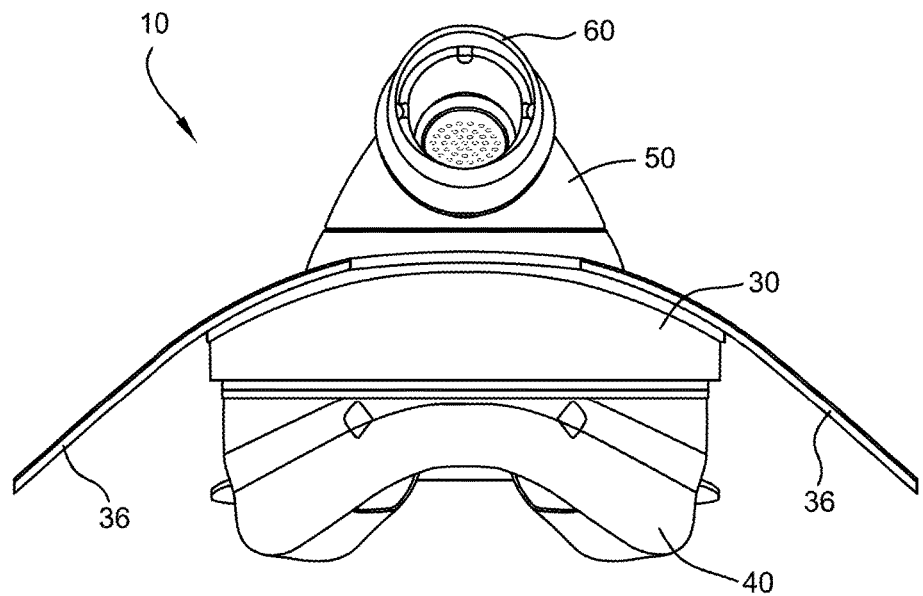

In the illustrated embodiment, the flexible or flexing portion 25 of the base 22 allows the forehead support 20 to flex from an original, unloaded position in opposing directions as shown in FIG. 5. In an embodiment, the forehead support 20 may flex up to 50 mm in either direction from its original unloaded position. The force displacement curve may have a linear relationship over the described displacement range.

In an embodiment, a force or load is applied to the forehead support (e.g., from headgear) to flex the forehead support from its original unloaded position to an operative or adjusted position. The forehead support may be resilient so that it substantially returns to its original unloaded position when not loaded. Alternatively, the forehead support may be deformable (e.g., plastically deformable, thermally deformable, malleable) so that it substantially retains its flexed or adjusted position when not loaded.

It should be appreciated that the original, unloaded position of the forehead support may vary. For example, the angle of the forehead support compared to the frame when no load is applied to the mask may be in the range depicted by a in FIG. 6. In an embodiment, a may be about 180°-220°, e.g., 200°.

1.2.1 Alternative Original, Unloaded Positions

In its original, unloaded position, the forehead support 20 may be designed to press against the patient's forehead, to sit away from the patient's forehead, or to meet the patient's forehead when no force is applied. These three alternative positions are depicted in FIGS. 7-1 to 9.

Figures 3, 4, 5, 6, 7:
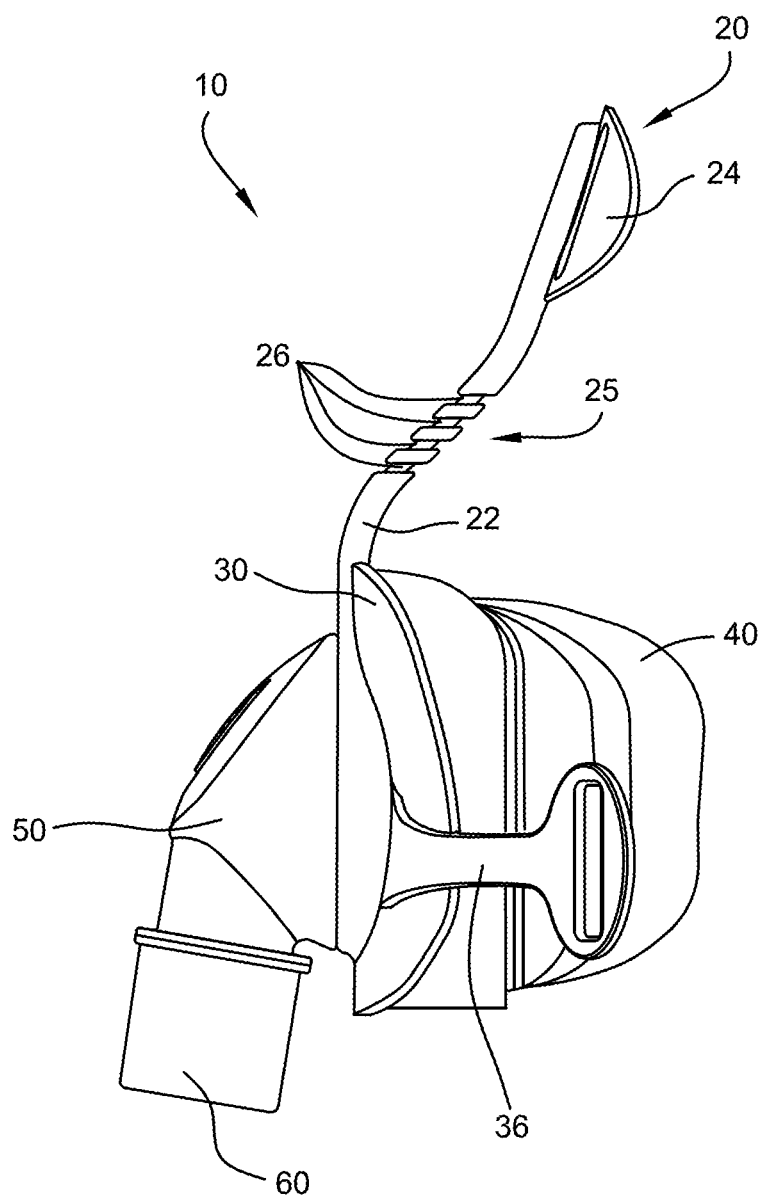

FIG. 7-1 illustrates a forehead support 20 that is oriented to sit away from the patient's forehead when no external force is applied. In use, as shown in FIG. 7-2, force from headgear tension or other external force in the direction indicated deflects the forehead support 20 until it is brought into contact with the patient's forehead and an equilibrium is reached between the patient's forehead and the forehead support 20, e.g., forehead padding. That is, the forehead support 20 is adjusted or flexed inwardly to fit to the patient's forehead.

Figures 1, 4:
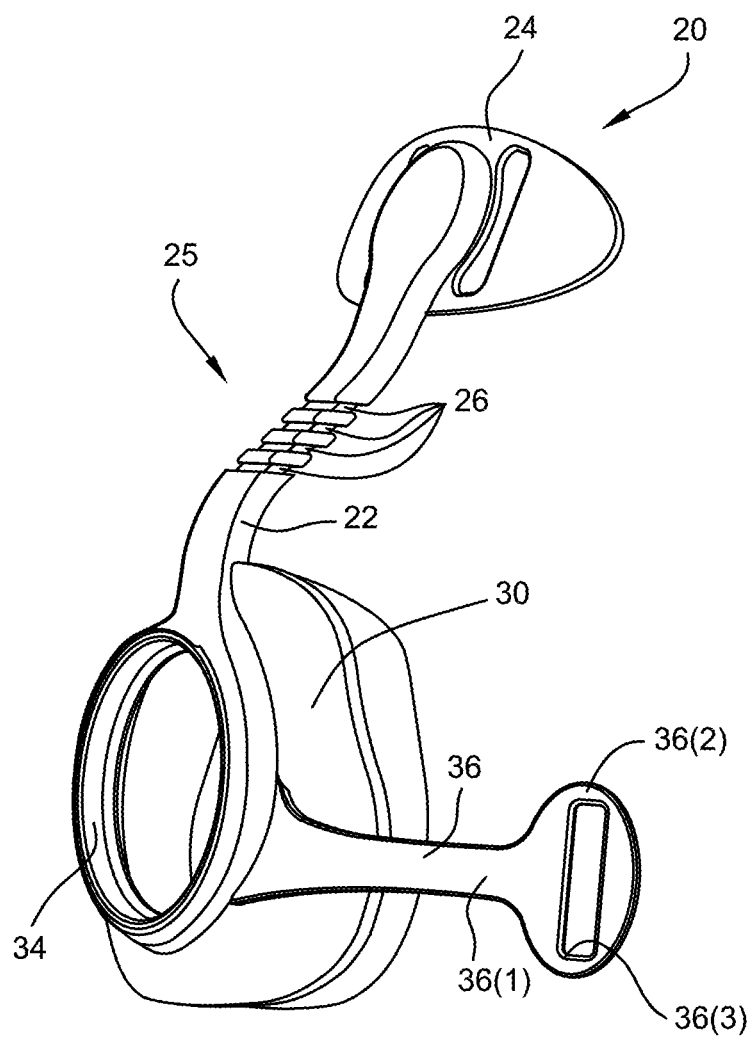
Figures 2, 4:
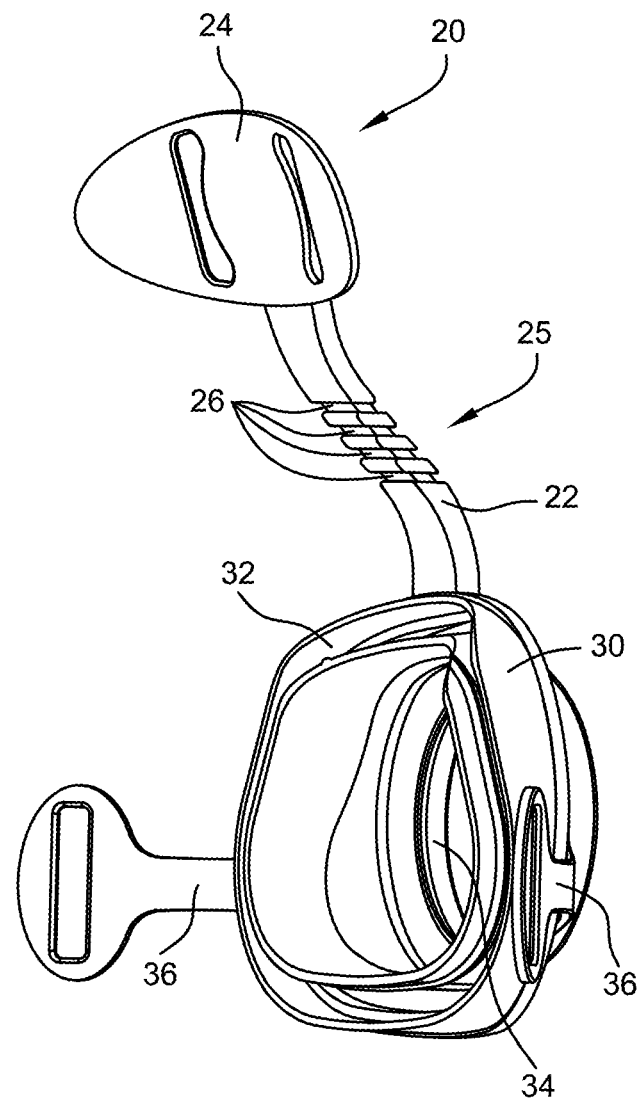
Figures 3, 4:
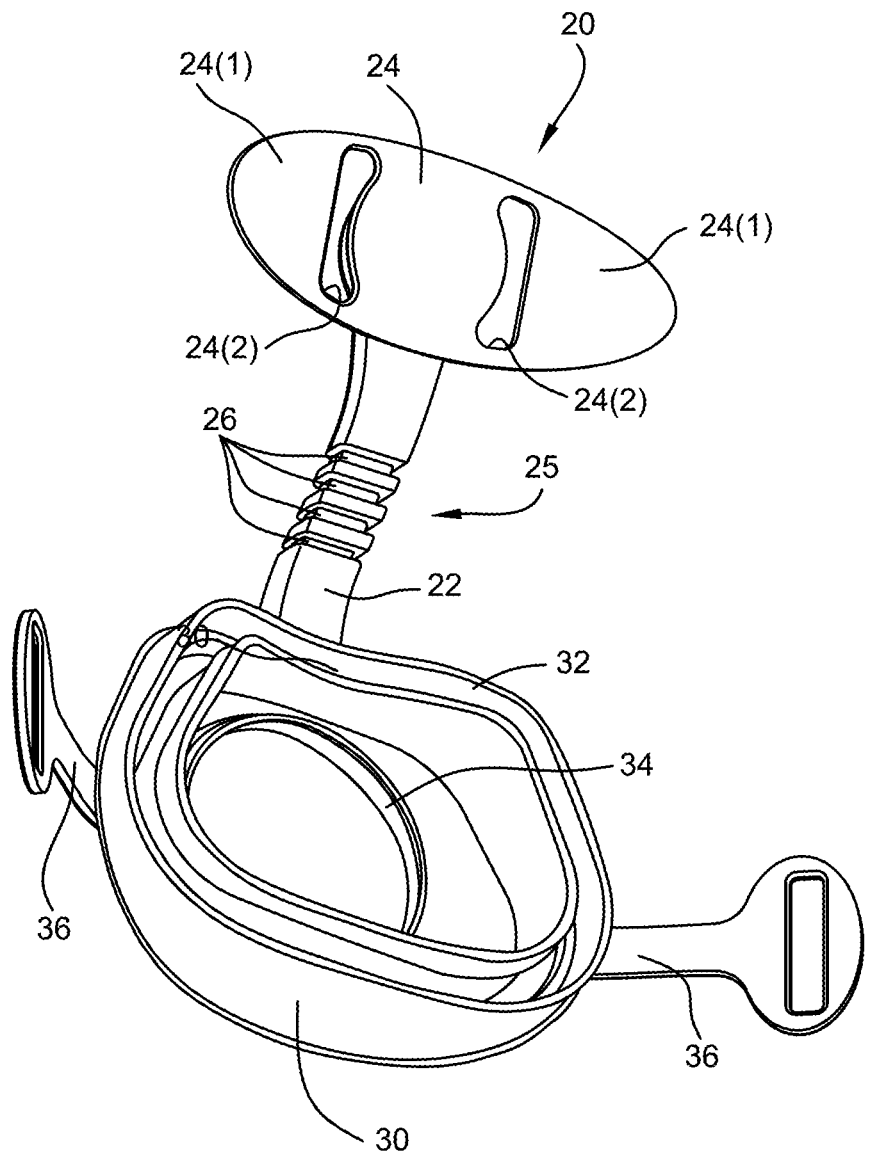
Figure 4:
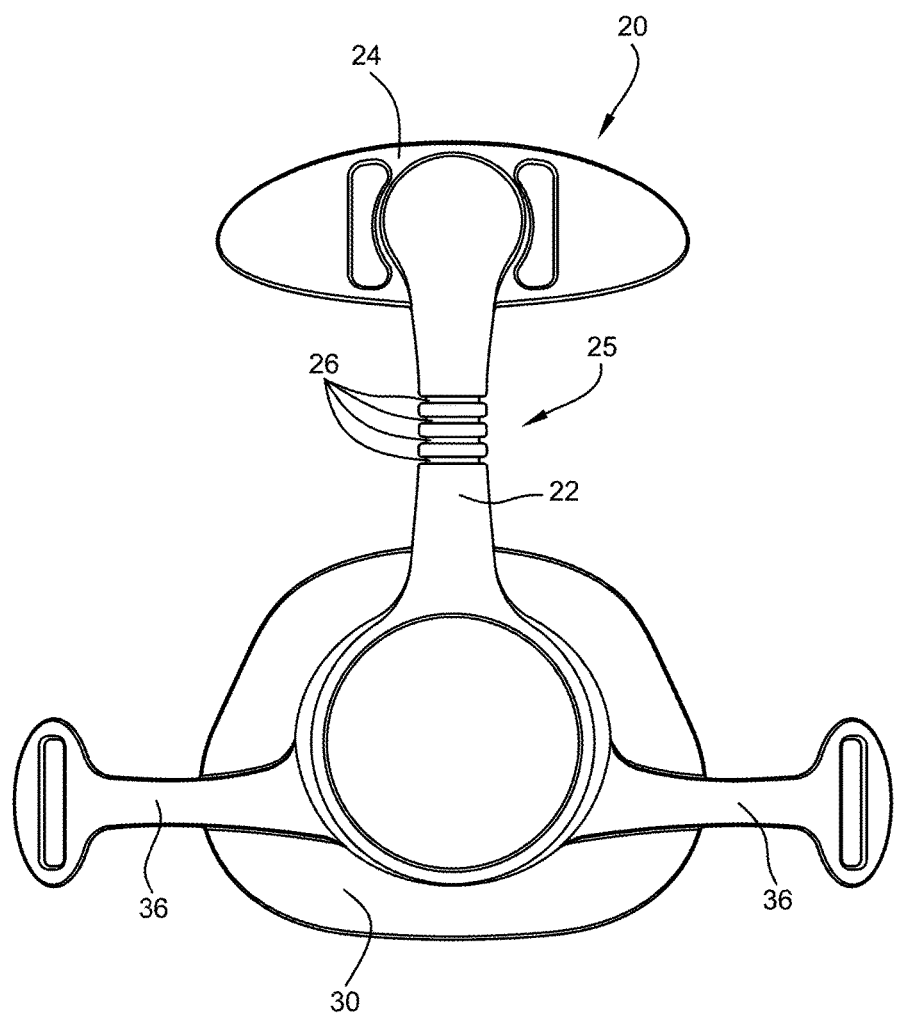
Figures 4, 5:
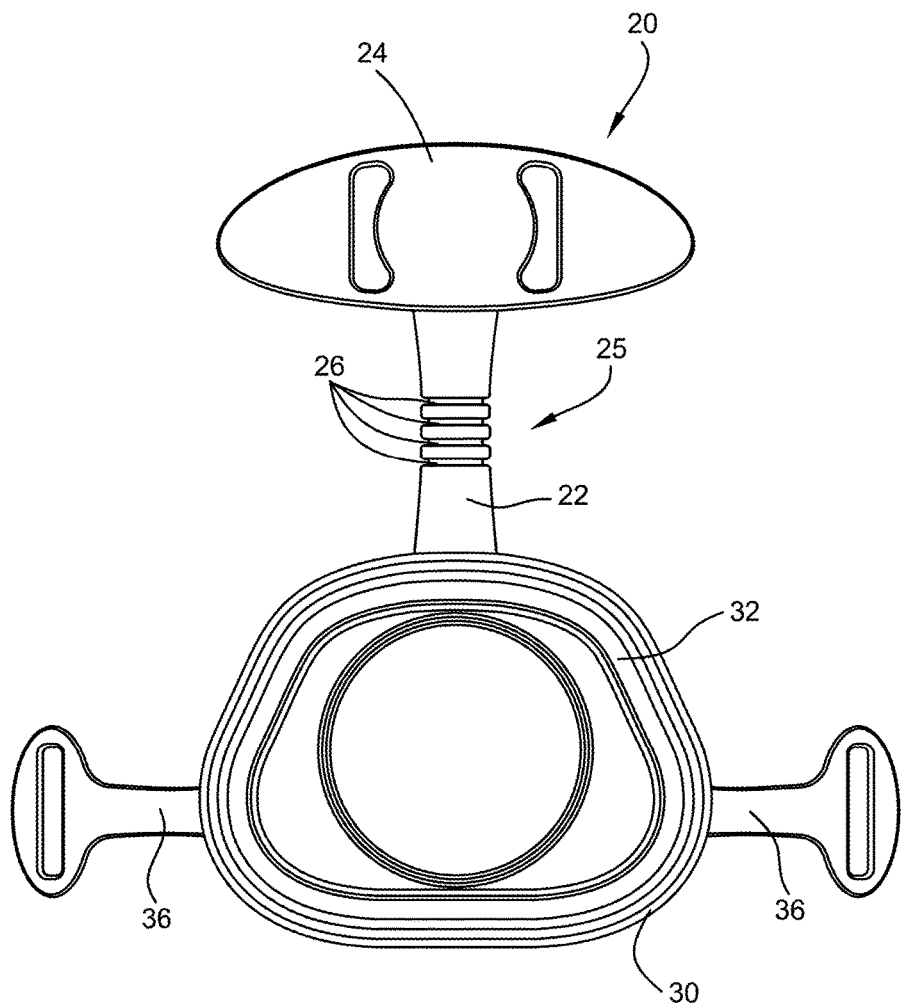
Figures 4, 5, 6:
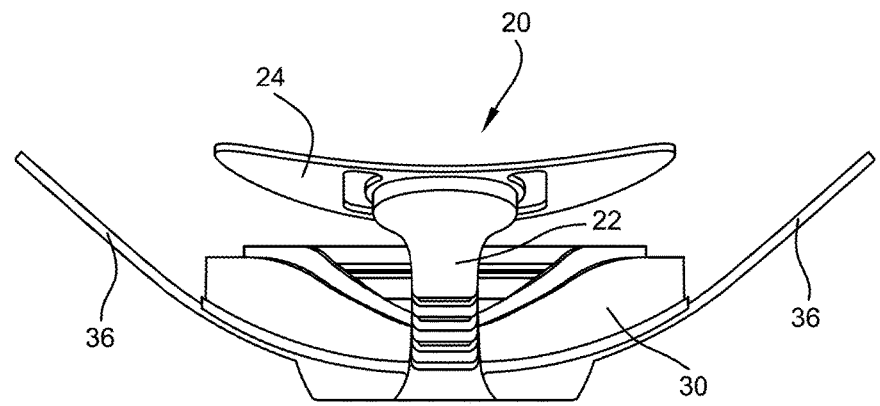
Figures 4, 5, 6, 7:
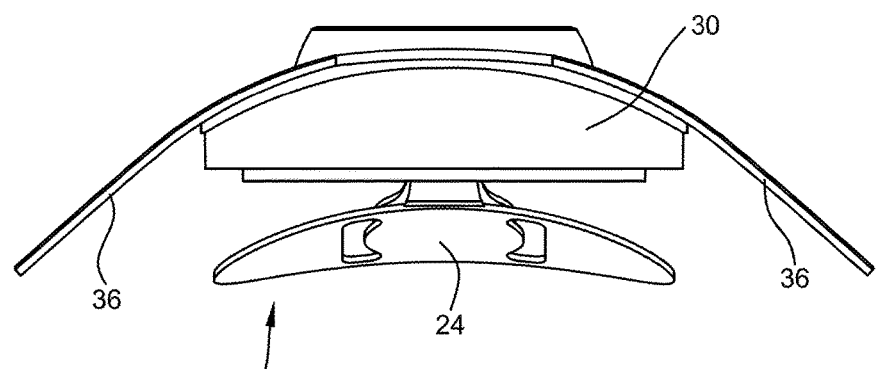
Figures 4, 5, 6, 7, 8:
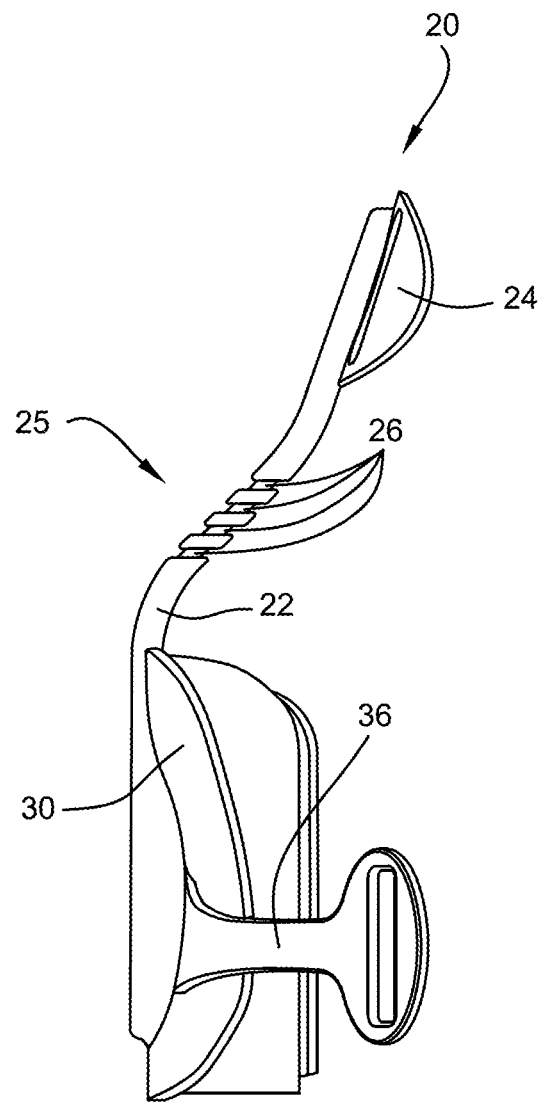
Figure 5:
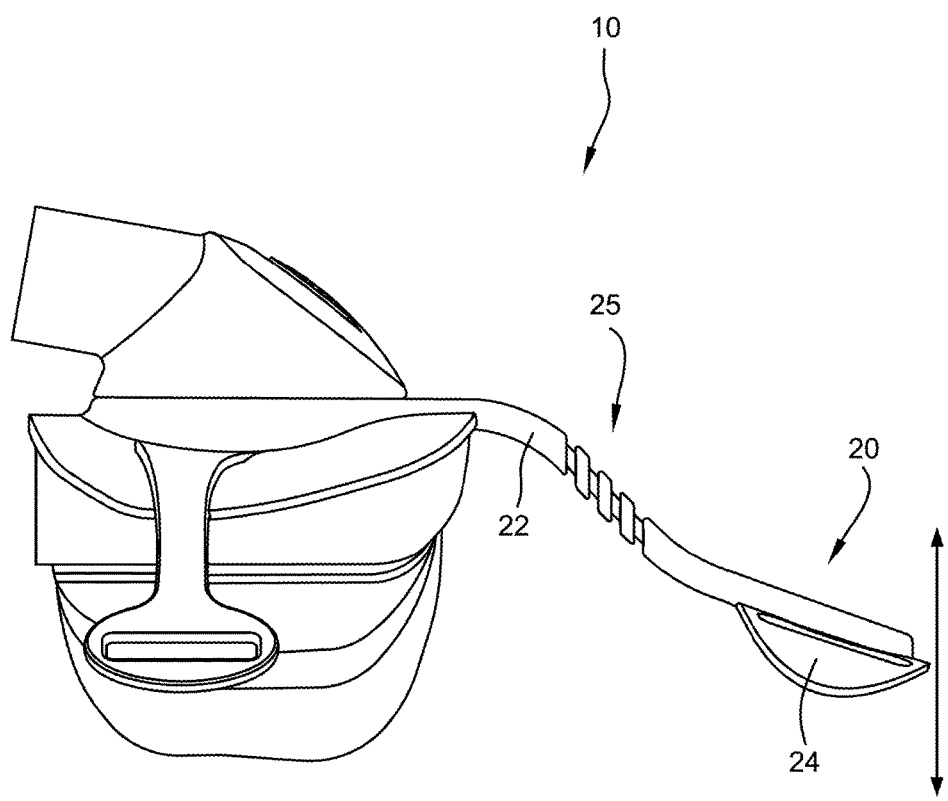
Figure 6:
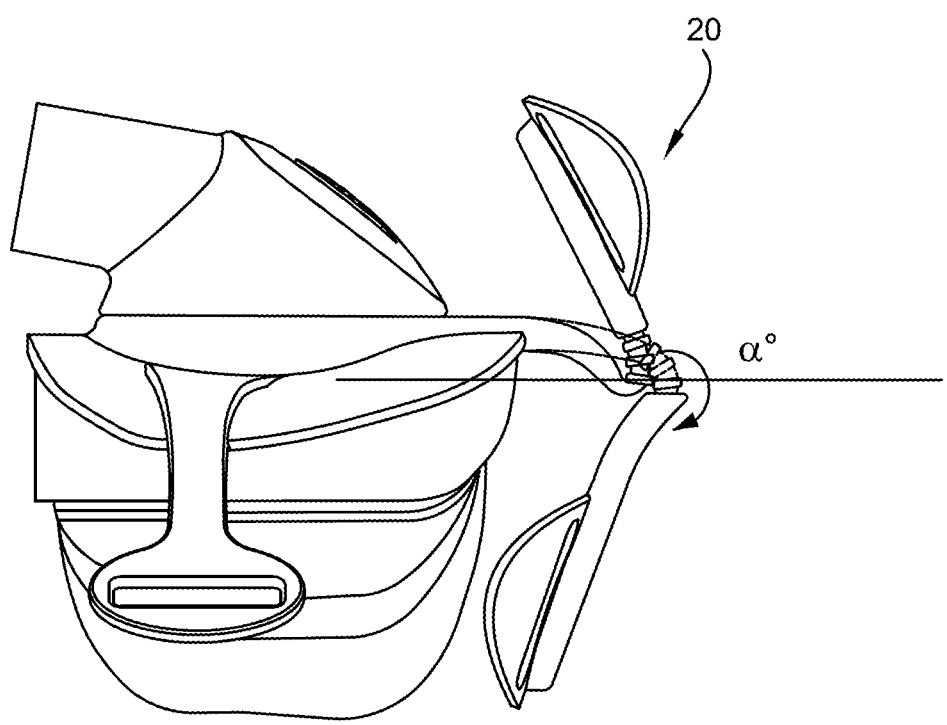
Figures 1, 7:
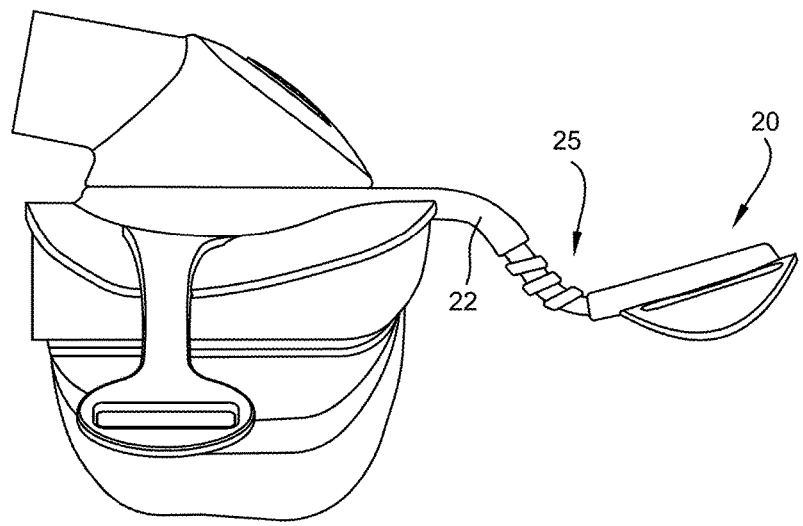
Figures 2, 7:
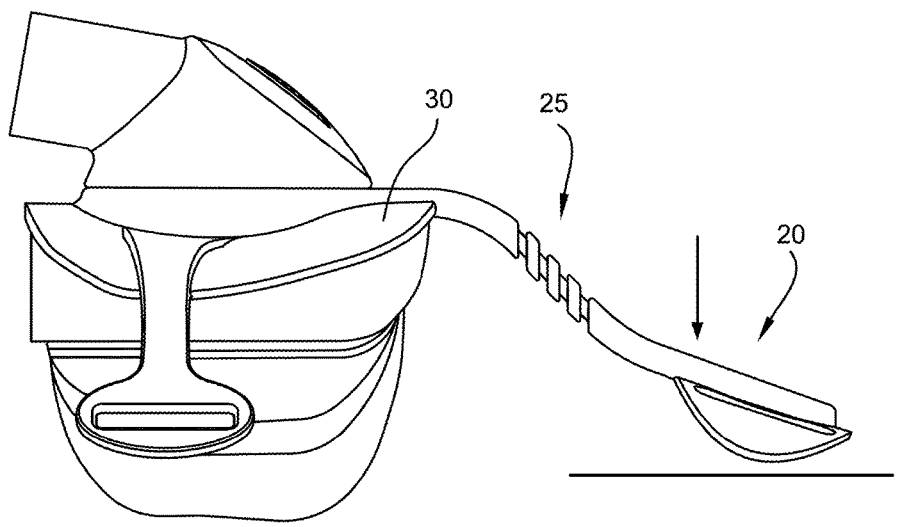
Figures 1, 8:
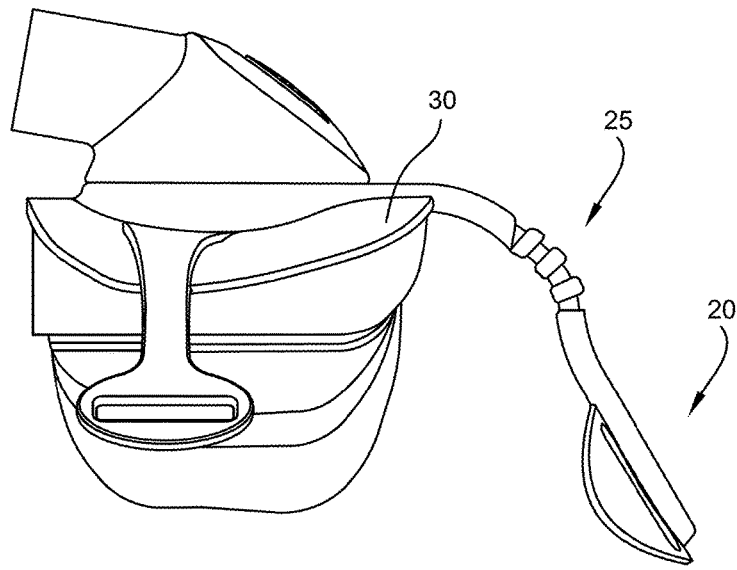
Figures 2, 8:
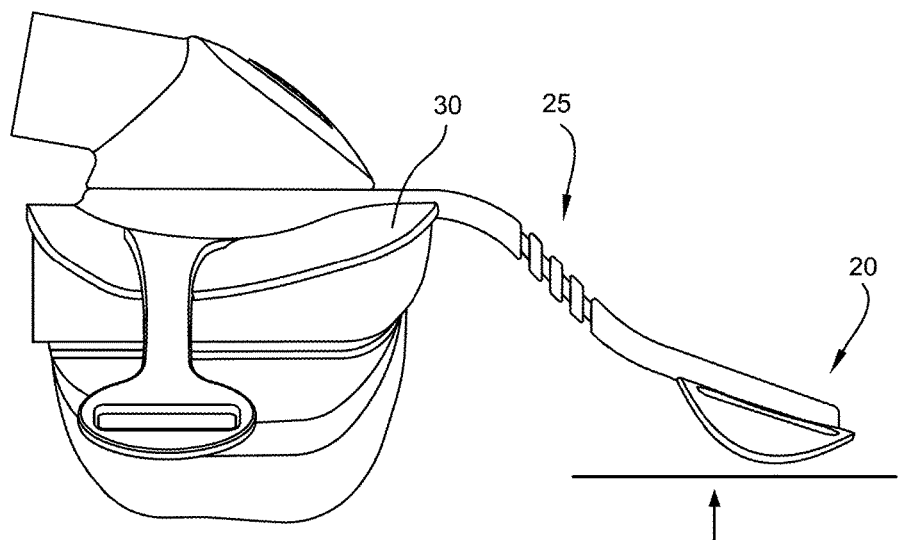

FIG. 8-1 illustrates a forehead support 20 that is oriented to decrease the angle between the forehead support 20 and the frame 30. When the mask is applied to the patient's face, as shown in FIG. 8-2, the forehead support 20 engages the patient's forehead and the reaction force from the patient's forehead in the direction indicated acts to flex the forehead support 20 away from the patient's face until equilibrium is achieved. In this arrangement, the spring force of the flexed forehead support 20 equals the reaction force from the patient's forehead. Thus, the mask provides maximum sealing on the patient's nose and the forehead support 20 is adjusted or flexed outwardly to fit to the patient's forehead.

Figure 9:
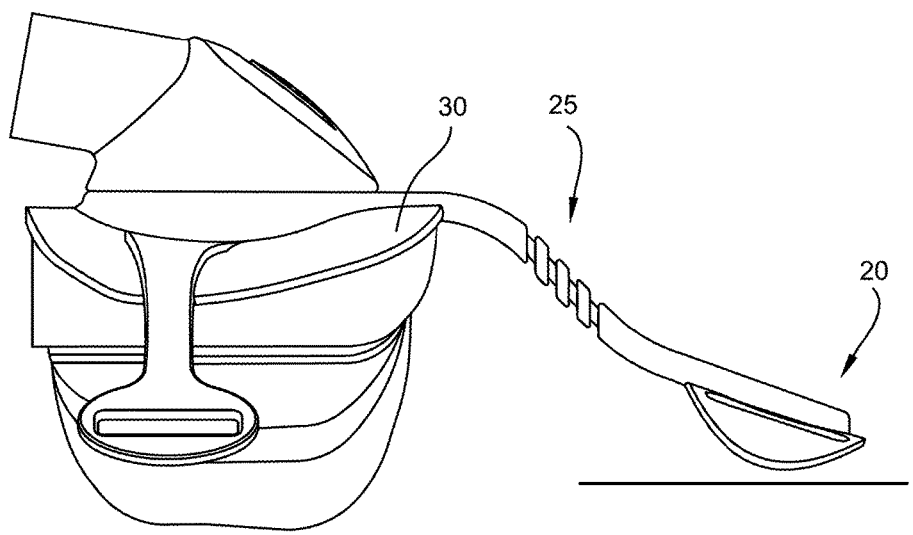
FIG. 9 is a side view of the mask shown in FIGS. 3-1 to 3-7 showing an orientation of the forehead support according to another embodiment of the present invention.

FIG. 9 illustrates a forehead support 20 that is oriented to closely align or match the forehead support 20 with the patient's forehead so that no deformation of the forehead support 20 is required or other components of the mask may accommodate for any differences in geometry. That is, the forehead support 20 is structured to engage and achieve equilibrium with the patient's forehead without flexing.

1.3 Spring Constant

The spring constant of the flexible forehead support 20 may be calculated by first determining the maximum amount of pressure that can be applied to the patient's forehead. The force is then equal to this pressure divided by the effective cross sectional area. The spring constant is equal to this force divided by the displacement of the forehead support. The displacement may be angular, linear, or a combination of both. Hence, the spring constant of the forehead support is equal to the desired force divided by the displacement of the forehead support.

That is:

$$T = Fr \text{ [Nm]}$$

$$T = -k\theta \text{ [Nm]}$$

$$P = F/A \text{ [Nm}^{-2}\text{]}$$

$$F = PA \text{ [N]}$$

$$F = T/r \text{ [N]}$$

$$F = -(k\theta)/r \text{ [N]}$$

$$k = -(Fr)/\theta \text{ [Nm/rad]}$$

Where, P=maximum acceptable pressure against patient's forehead;
F=maximum force of forehead support against patient's forehead;
A=effective cross-sectional area of the forehead support that contacts the patient's forehead;
k=spring constant of flexible forehead support;
T=torque
θ=Angular displacement of forehead support from relaxed to deformed position; and
r=length of forehead support after the flexing location.

Figure 10:
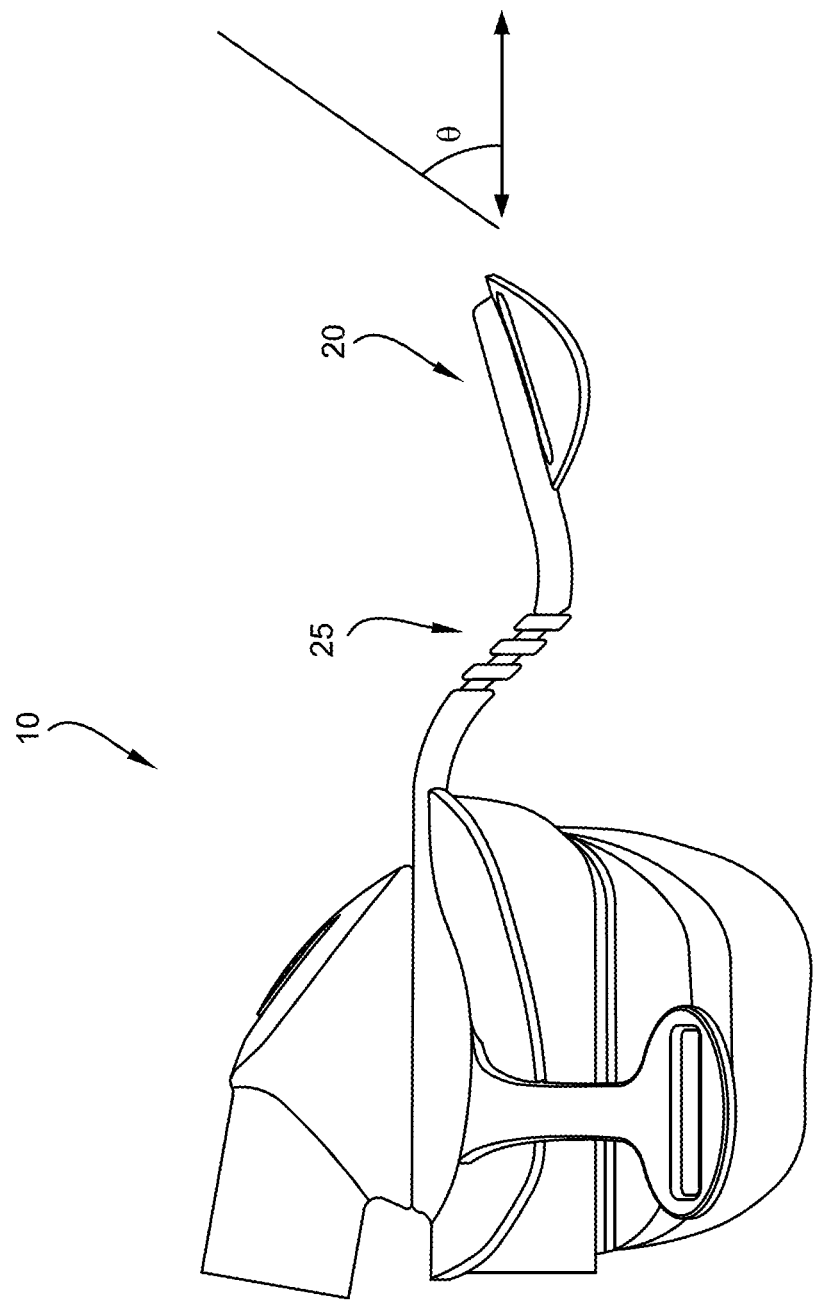
FIG. 10 is a side view of the mask shown in FIGS. 3-1 to 3-7 showing a spring constant variable of the forehead support according to an embodiment of the present invention.
Figure 11:
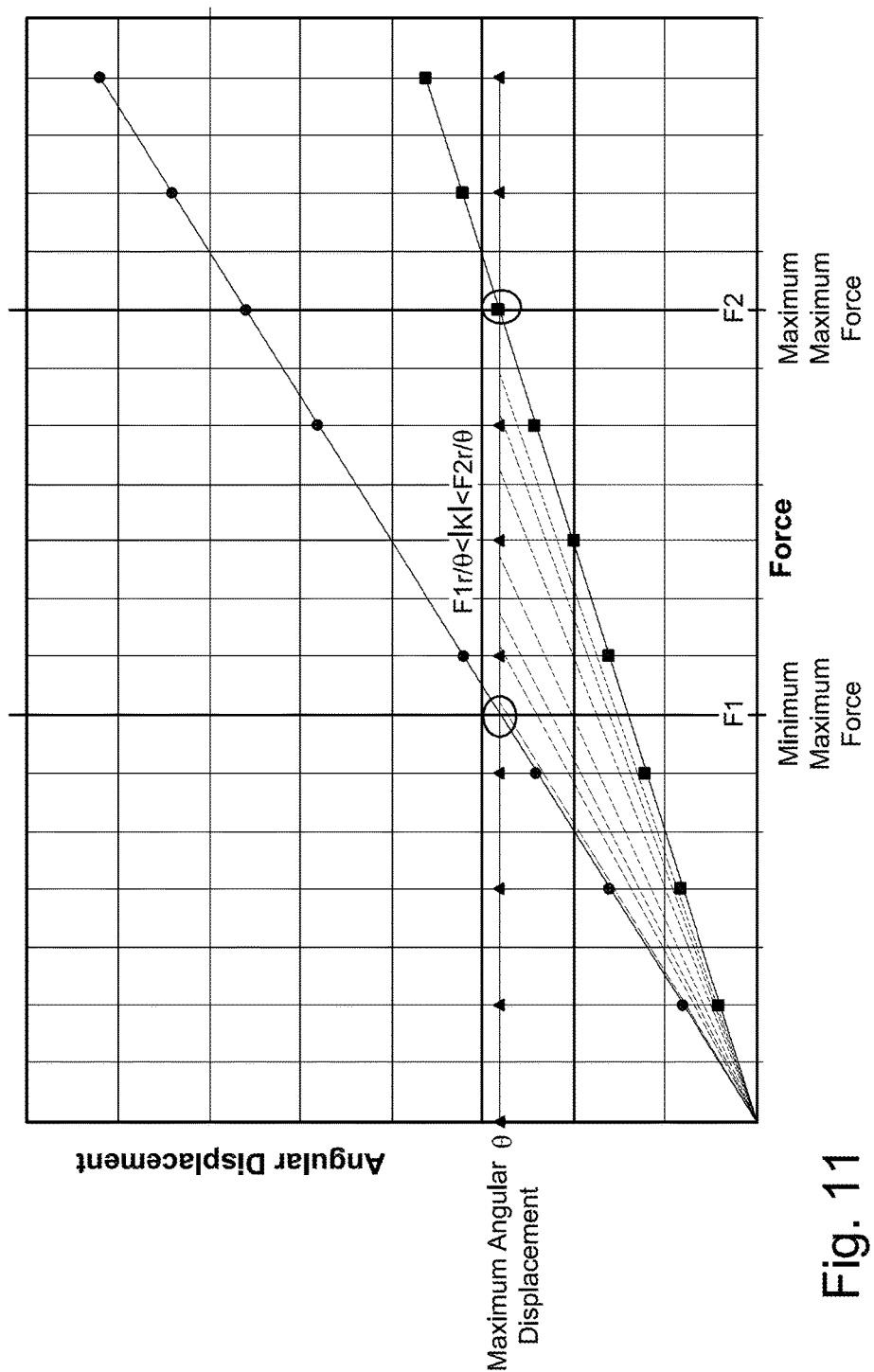
FIG. 11 is a graph showing a range of spring constants of the forehead support according to an embodiment of the present invention.

FIG. 10 illustrates the variable θ described above. A range of maximum forces may be used to provide a range of acceptable spring constants as shown in FIG. 11. That is, FIG. 11 illustrates a range of acceptable spring constants with one end of the range having a spring constant that passes through a minimum value for the maximum force (F1) at maximum angular displacement and the other end of the range having a spring constant that passes through a maximum value for the maximum force (F2) at maximum angular displacement.

1.4 Limited Axial Rotation

Figure 12:
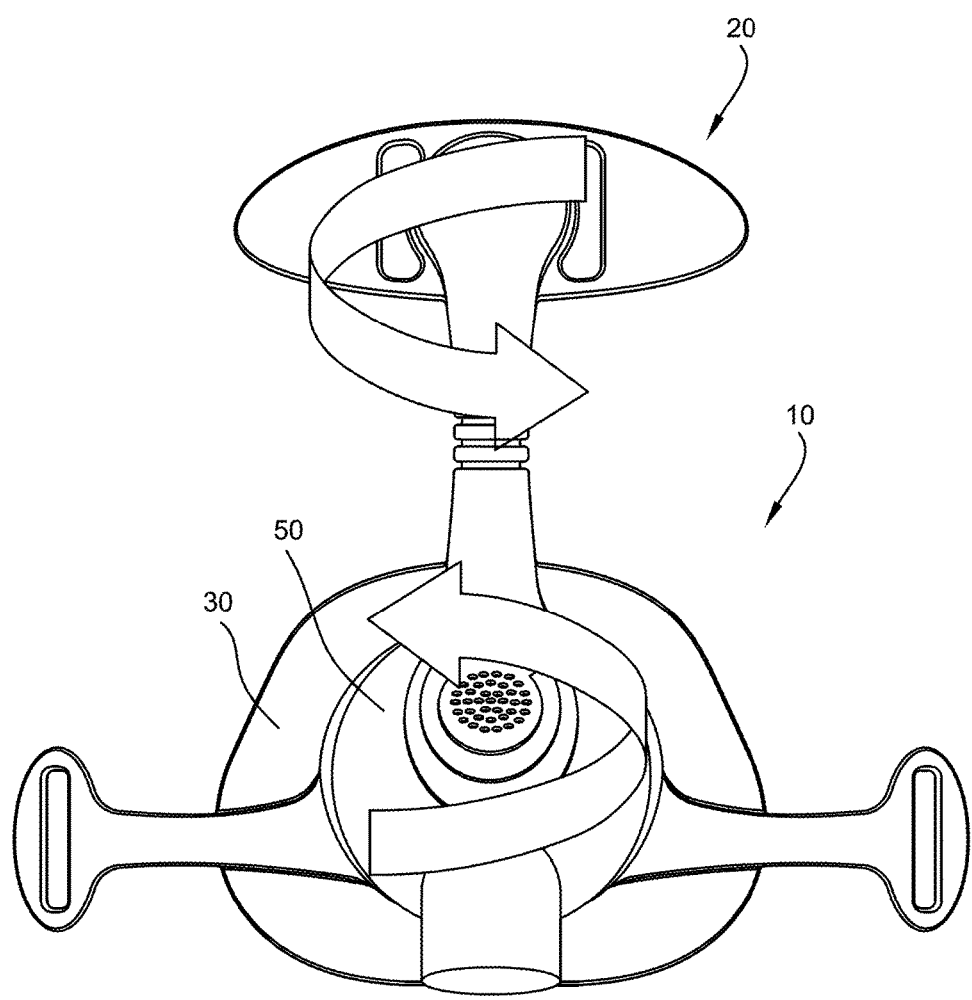
FIG. 12 is a front view of the mask shown in FIGS. 3-1 to 3-7 showing limited axial rotation of the forehead support according to an embodiment of the present invention.

As shown in FIG. 12, the forehead support 20 is structured to provide flexibility but limit the amount of axial rotation or axial twist (as indicated by arrows) that is possible between the portion of the forehead support 20 that contacts the patient's forehead and the frame 30. This arrangement prevents instability due to rotation about the median plane, which can adversely affect the seal. For example, the width and/or height of the forehead support 20 may be controlled to minimize axial twist.

1.5 Control of Flexibility

Flexibility provided by the forehead support 20 may be controlled by varying different aspects of the base 22 of the forehead support 20. For example, the material, dimensions, and/or configuration of the base 22 may be adjusted to adjust the flexibility.

1.5.1 Cross-sectional Thickness

Figure 13:
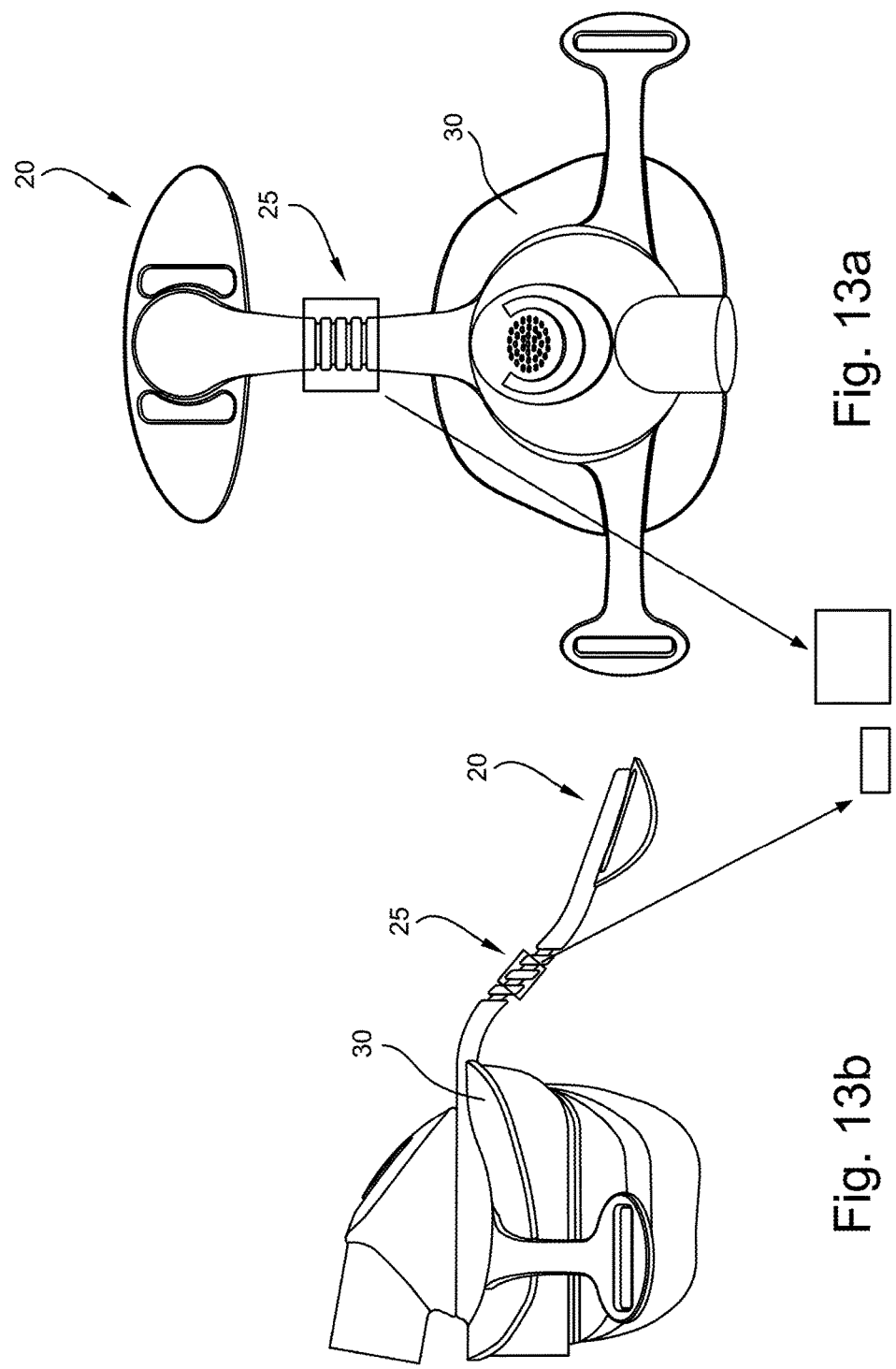
FIGS. 13a and 13b are front and side views of the mask shown in FIGS. 3-1 to 3-7 illustrating various cross-sectional thicknesses of the forehead support according to an embodiment of the present invention.

In an embodiment, the flexibility of the forehead support 20 and the location of the flexibility may be controlled by varying the cross-sectional thickness of the forehead support 20 in the medial plane. For example, controlled flexibility may be achieved by having a forehead support 20 in which the cross-section in the frontal plane (FIG. 13*a*) is thicker than the cross-section in the medial plane (FIG. 13*b*).

1.5.2 Recesses

In the illustrated embodiment, the base 22 of the forehead support 20 includes one or more horizontally extending recesses or cut-outs 26 along a portion of the length thereof, e.g., s FIGS. 3-1 to 4-8. As illustrated, the flexible portion 25 of the base 22 includes four spaced-apart and horizontally aligned recesses 26, each recess 26 extending about a perimeter of the base 22. The recesses 26 may have any suitable width and depth to control flexing of the forehead support. That is, the recesses 26 control the amount and location of flexing of the forehead support by controlling the cross-sectional thicknesses in the frontal and medial planes.

However, the one or more recesses may have other configurations to provide flexibility, e.g., extend partially around the perimeter, vertically extending.

In addition, the recesses emphasize or provide a visual indication to the patient that flexing of the forehead support can occur.

In this embodiment, the forehead support is resilient so that it substantially returns to its original unloaded position when not loaded, e.g., from headgear.

1.5.3 Ridges

Figure 14:
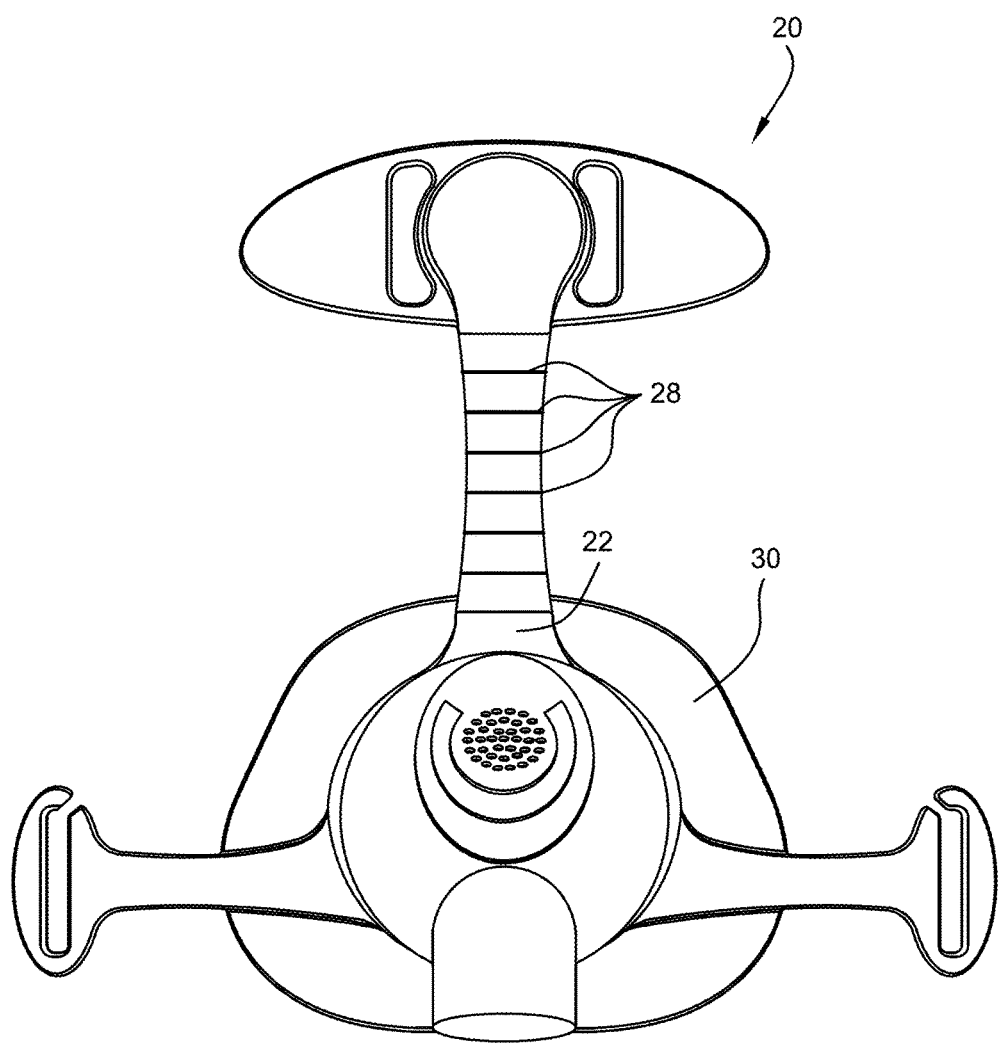
FIG. 14 is a front view of a mask including a forehead support with horizontal ridges according to an embodiment of the present invention.

In another embodiment, the axial rotation shown in FIG. 12 may be limited by placing one or more horizontal ridges 28 along all or some of the length of the base 22 of the forehead support 20, as shown in FIG. 14. This again controls the amount and location of the flexing of the forehead support by controlling the cross-sectional thicknesses in the frontal and medial planes. The ridges 28 may be comolded with the base 22 and may have other suitable configurations to promote bending in a particular area, e.g., S-shaped.

1.6 Elbow

Figures 1, 15:
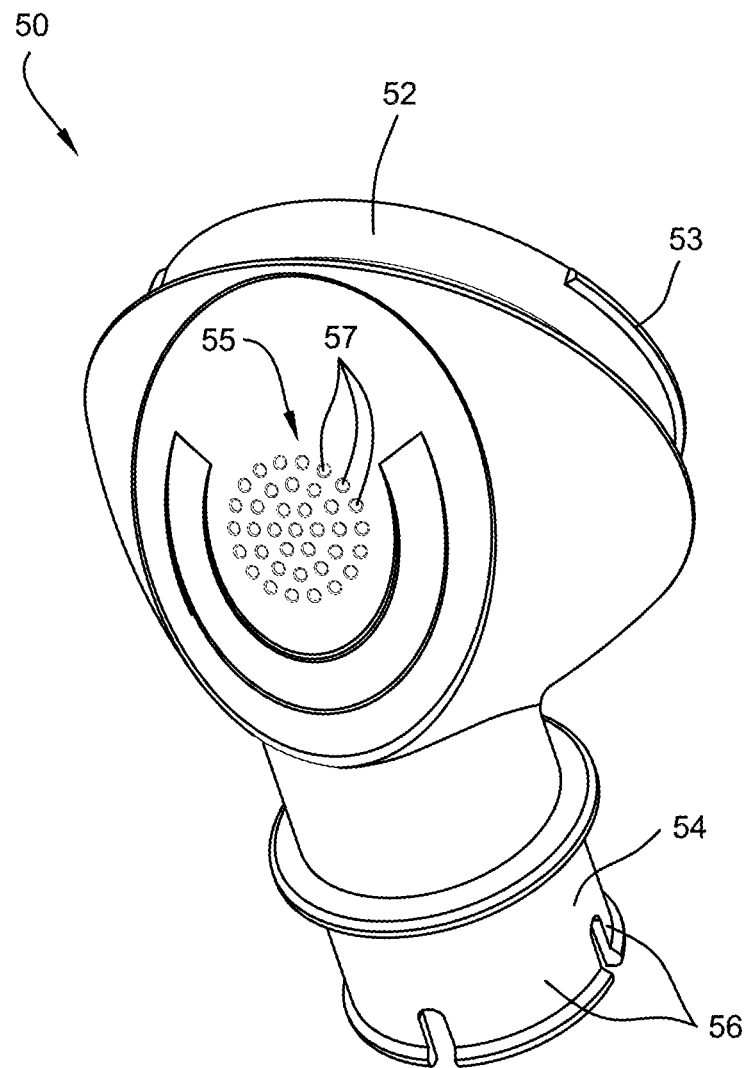
Figures 2, 15:
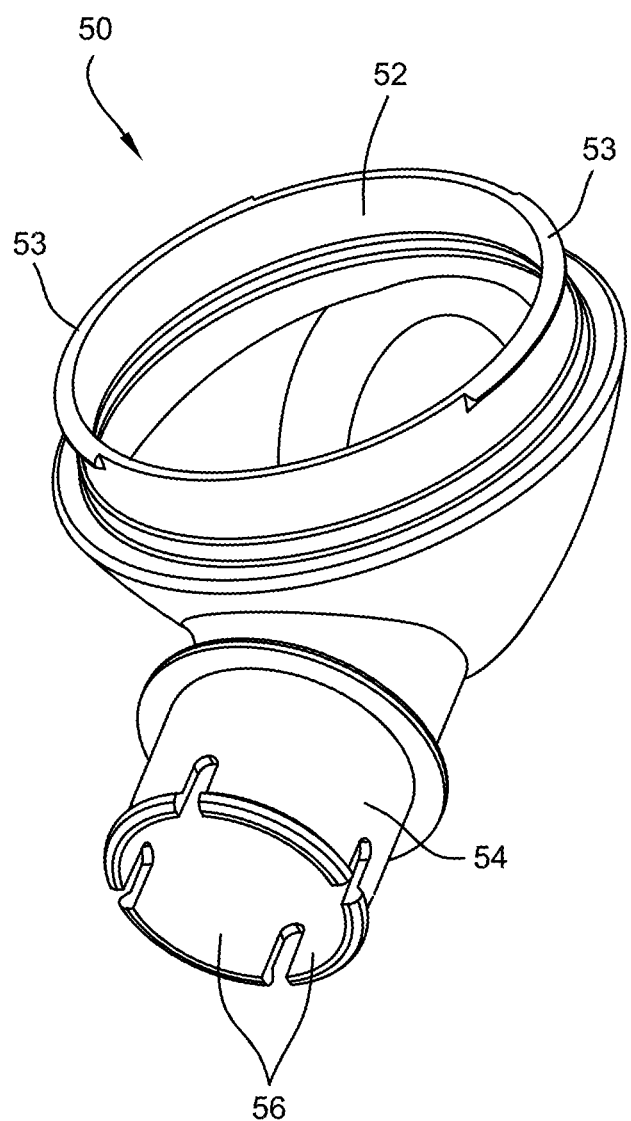
Figures 3, 15:
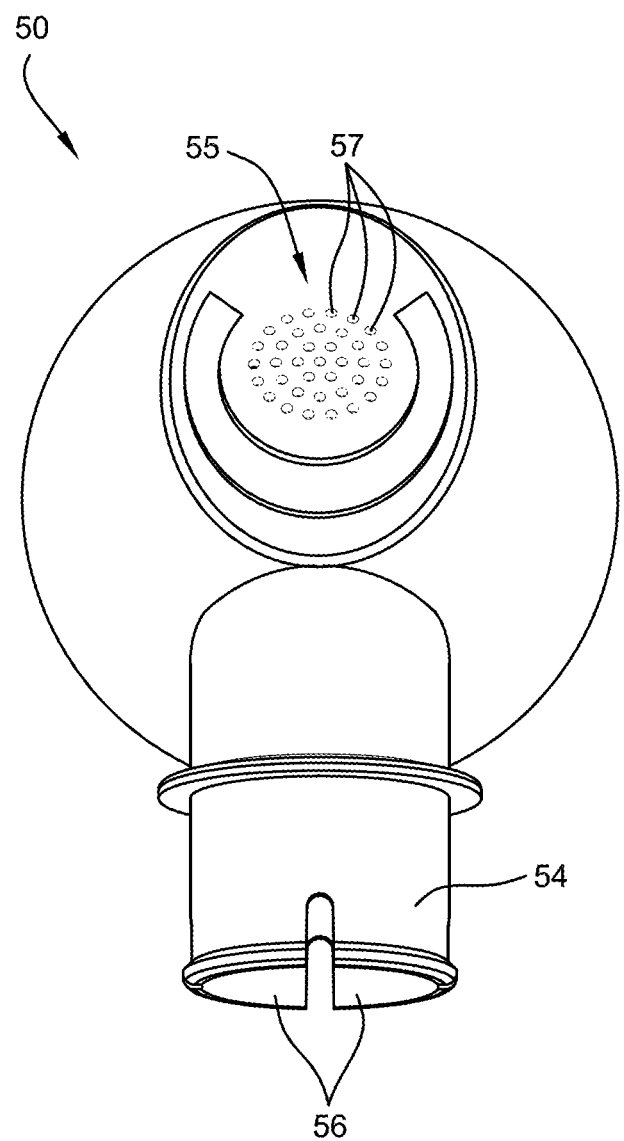
Figures 4, 15:
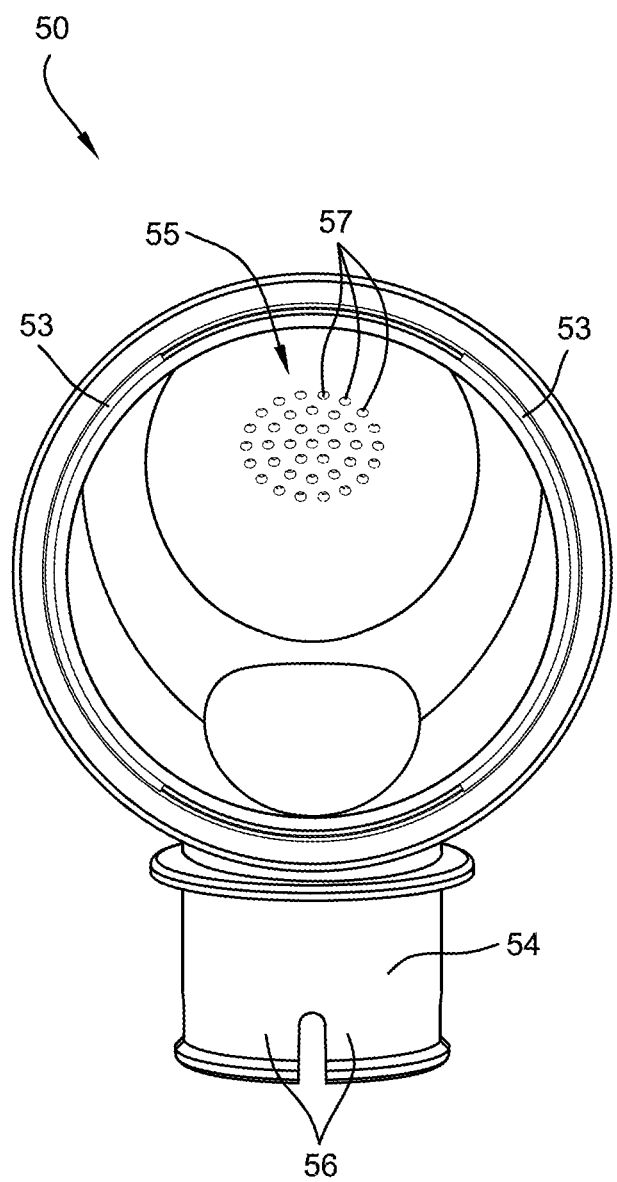
Figures 5, 15:
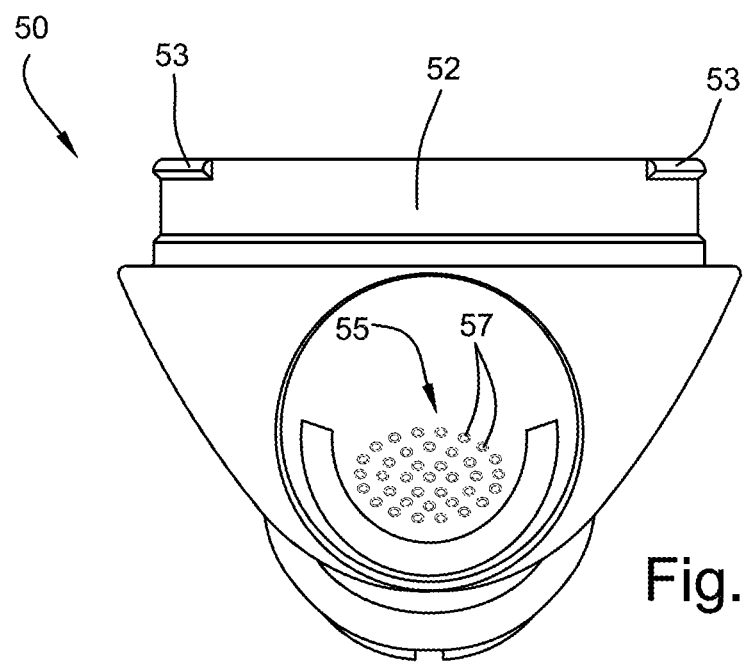
Figures 6, 15:
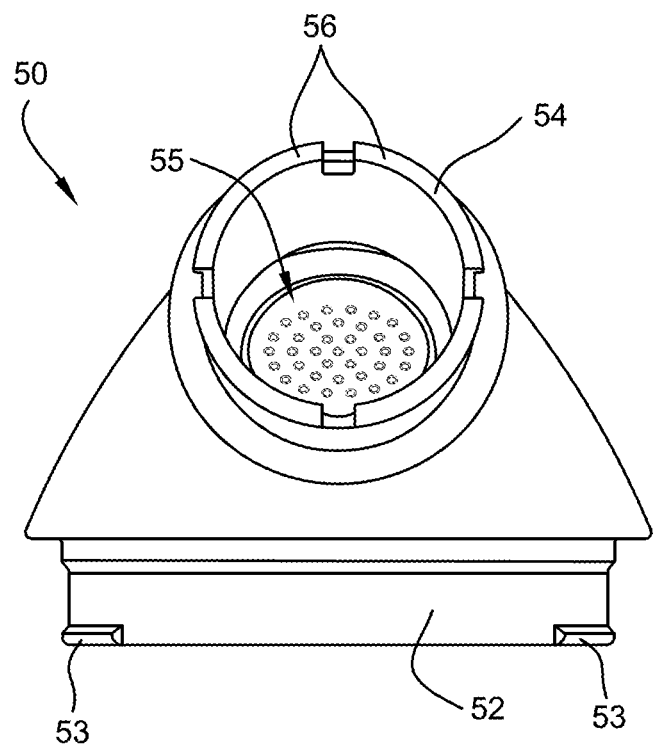
Figures 7, 15:
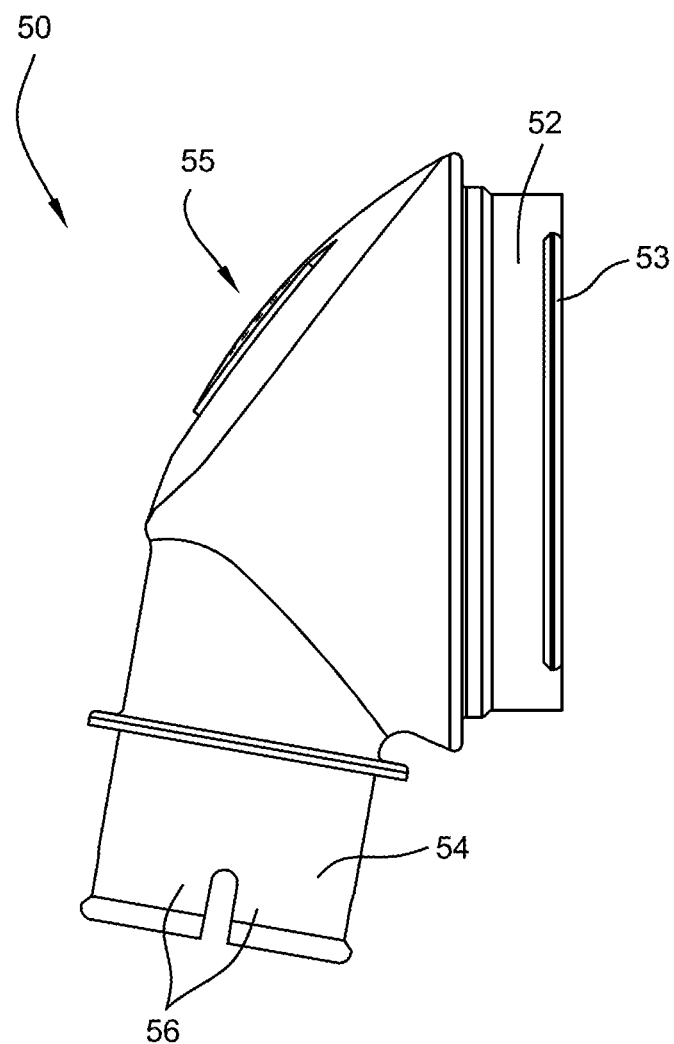
Figures 8, 15:
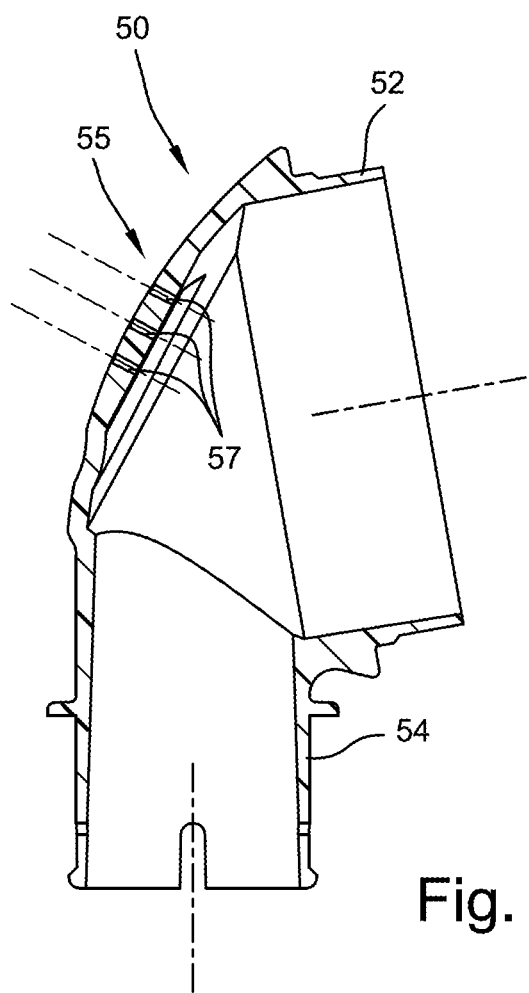
Figures 9, 15:
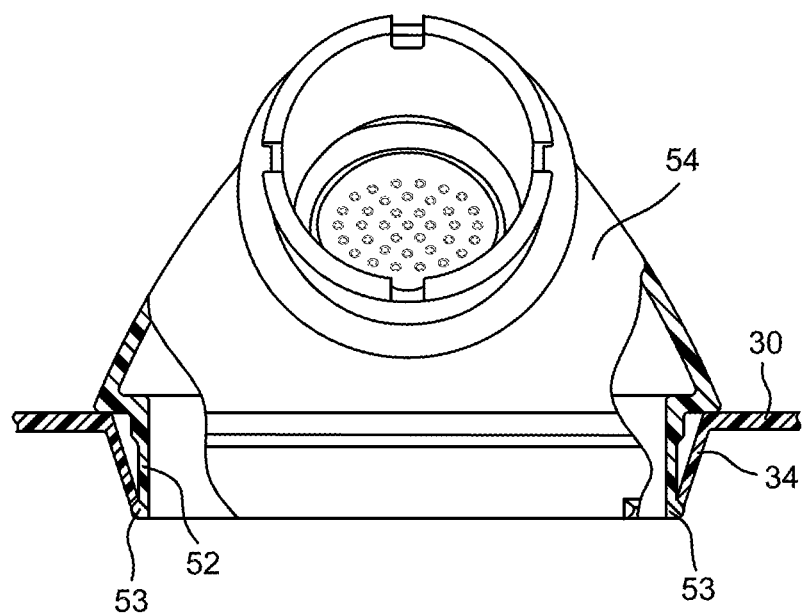

FIGS. 15-1 to 15-8 illustrate an elbow 50 of the mask 10. The elbow 50 includes a first portion 52 structured to interface or otherwise attach to the frame 30 and a second portion 54 provided to a swivel joint 60 (e.g., see FIGS. 16-1 to 16-4) adapted to be connected to an air delivery tube. In addition, the elbow 50 includes a vent arrangement 55 for gas washout. As illustrated, the elbow 50 provides a relatively low profile, and tapers from a larger internal diameter at the first portion 52 to a smaller internal diameter at the second portion 54 (e.g., see FIG. 15-8).

1.6.1 Frame Attachment

In the illustrated embodiment, the first portion 52 includes opposing flanges or beads 53 along its peripheral edge that are adapted to interface with or otherwise removably connect to the tube portion 34 of the frame 30, e.g., with a snap-fit. As shown in FIG. 15-9, the tube portion 34 includes a generally part conic shape in which it converges from a larger (outside) diameter to a smaller (inside) diameter. This arrangement facilitates insertion of the elbow 50 into the tube portion 34 and provides an interference fit to substantially seal the elbow 50 to the frame 30. That is, the tube portion 34 is biased radially into the elbow 50 to provide a connection that allows swivel-type movement but prevents leak in use. However, other suitable arrangements for attaching the elbow 50 to the frame 30 are possible.

1.6.2 Swivel Joint Attachment

Figures 1, 16:
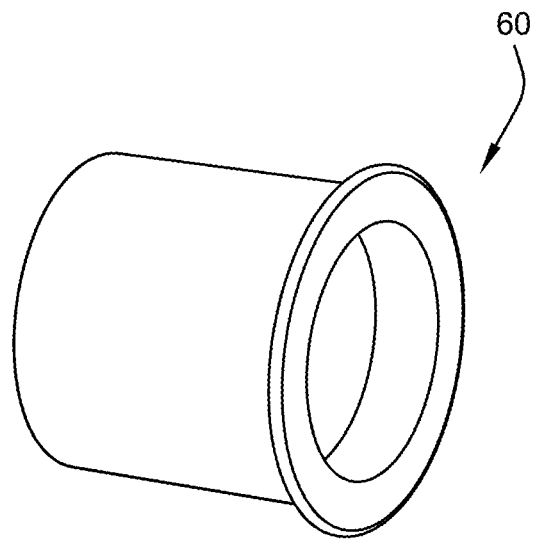
Figures 2, 16:
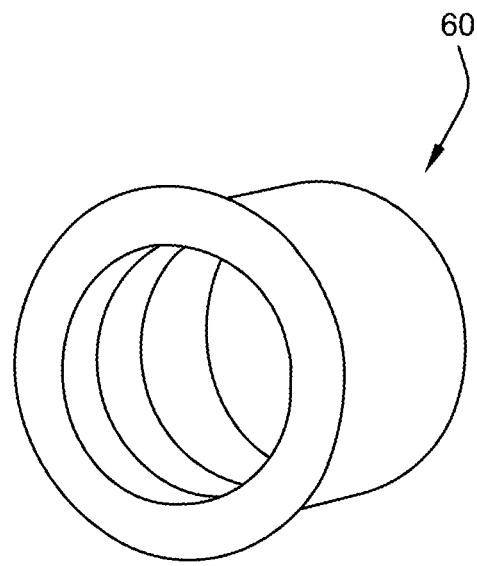
Figures 3, 16:
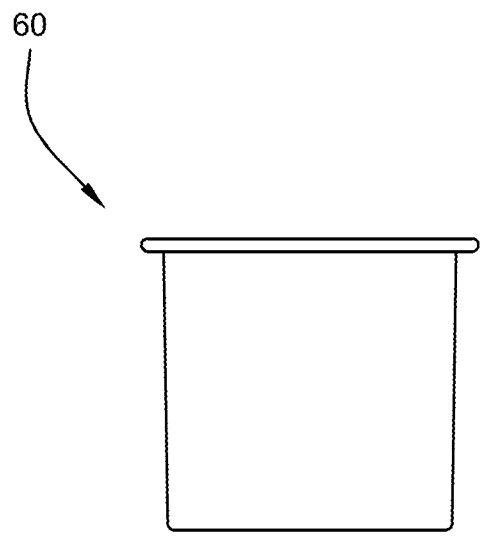
Figures 4, 16:
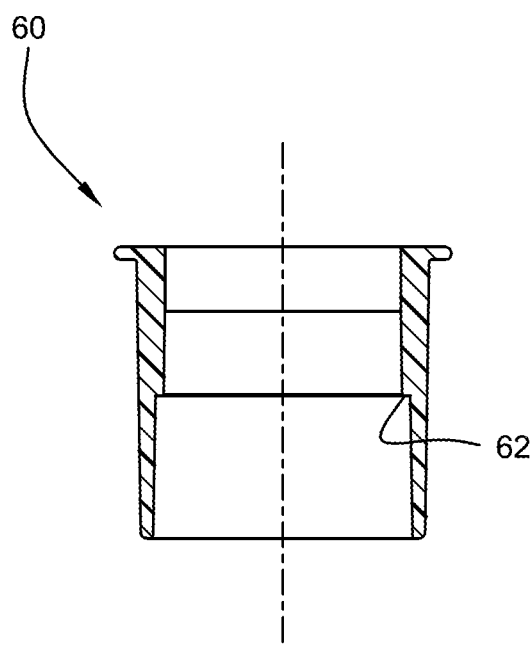

The second portion 54 includes snap-fit tabs 56 to connect the second portion 54 to the swivel joint 60. As shown in FIG. 16-4, the internal surface of the swivel joint 60 provides a shoulder 62 to engage the snap-fit tabs 56.

1.6.3 Vent Arrangement

In the illustrated embodiment, the vent arrangement 55 of the elbow 50 is positioned on a slightly contoured surface of the elbow 50 (e.g., see FIG. 15-7). As illustrated, the vent arrangement 55 includes a plurality of orifices 57 arranged in concentric circles, e.g., central orifice with concentric circles of orifices arranged about the central orifice.

Each orifice 57 may have a cylindrical configuration (e.g., see FIG. 15-8). Alternatively, each orifice may have a generally part conic shape, including opposed walls that converge from a larger (inside) diameter to a smaller (outside) diameter, as viewed in the direction of exhausted gas.

However, it should be appreciated that the vent arrangement 55 may include other suitable hole configurations, hole arrangements, hole numbers, and/or hole shapes.

2. Second Embodiment of Forehead Support

Figures 3, 17:
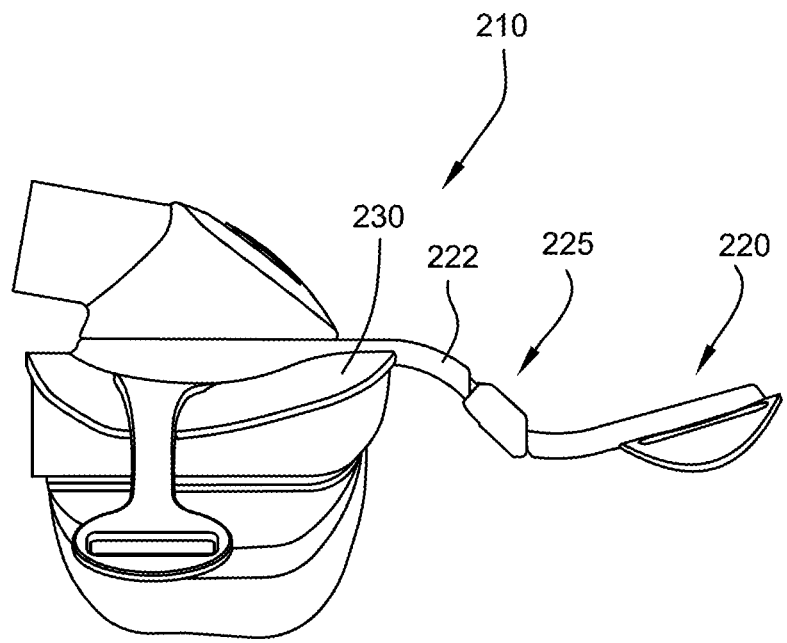
Figures 4, 17:
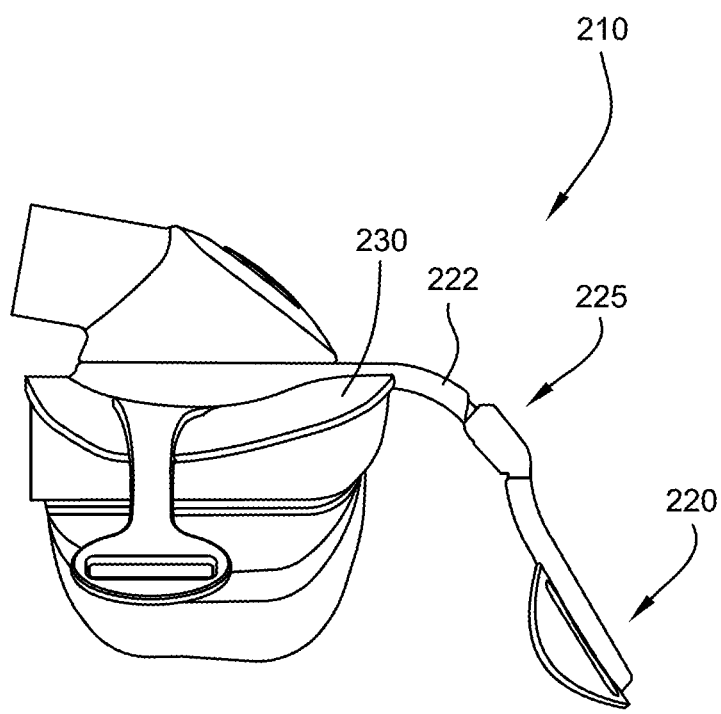

FIGS. 17-1 to 17-4 illustrate a respiratory mask 210 including a forehead support 220 according to another embodiment of the present invention. In this embodiment, the forehead support 220 may be manufactured from two or more materials to produce a single forehead support element.

As illustrated, the base 222 of the forehead support 220 is constructed of two different materials, i.e., an intermediate portion 225 of the base 222 is constructed of a different material than the remainder of the base (e.g., elastic material or properties). Depending on the degree of stiffness of each material, which can be determined from the Young's modulus of the material, and the location of the different materials the amount of flex and the location of the flexion can be controlled.

In the illustrated embodiment, the Young's modulus of the intermediate portion 225 is lower than the rest of the forehead support 220. As a result, the forehead support 220 is configured to bend at this intermediate location when force is applied to the forehead support. FIGS. 17-3 and 17-4 illustrate the forehead support 220 in first and second deformed positions with respect to the frame 230.

The forehead support 220 may be manufactured in one piece using numerous techniques, e.g., overmolding, comolding, or dual shot injection molding. Alternatively, the different components of the forehead support 220 may be manufactured separately and a second process (e.g., the use of adhesives or ultrasonic welding) may be used to combine these different components into a single element.

In an embodiment, the intermediate portion of the forehead support may be resilient so that the forehead support substantially returns to its original unloaded position when not loaded. Alternatively, the intermediate portion of the forehead support may be deformable (e.g., plastically deformable) so that it substantially retains its flexed or adjusted position when not loaded.

3. Third Embodiment of Forehead Support

Another embodiment includes a flexible forehead support that is structured to allow easy adjustment by the user. In this embodiment, some or all of the forehead support is manufactured from a material (e.g., polycarbonate (e.g., cold formed), polypropylene, nylon) that can be plastically deformed into the correct shape using external forces (e.g., manually deform into desired shape). That is, the forehead support may be plastically deformed into a desired position. The forehead support is then able to deform elastically as it is worn by the patient, hence providing a close fitting forehead support that dynamically adapts to the relative movement of the frame and the patient's forehead thus not disturbing the seal.

This embodiment may be manufactured from one or more materials. One possible embodiment includes a malleable wire or metal component that is overmolded with a soft, flexible material (e.g., TPE like material).

In this embodiment, the forehead support is deformable (e.g., plastically deformable, malleable) so that it substantially retains its flexed or operative orientation when not loaded.

4. Fourth Embodiment of Forehead Support

Another embodiment relates to a forehead support in which some or all of the forehead support is constructed of a material that can be thermally deformed using hot water or some other heating element (e.g., light, heat) to achieve the desired adjustment. That is, at least the base of the forehead support may be constructed of a thermoforming plastic material that can be bent or otherwise self deform to the desired position (e.g., flow into contours of the patient's face) when heated up and then sets into such desired position when cooled. This allows a customized, fixable position for the forehead support.

In an embodiment, once the forehead support had cooled, it would still retain some ability to flex and/or conform to the patient's head. Also, in an embodiment, the thermal deformation may be repeatable so that the forehead support may be thermally deformed one or more times to change or update the position of the forehead support.

In an alternative embodiment, at least the base of the forehead support may provide a flexible region with a bladder of epoxy. The epoxy is released in a suitable manner (e.g., remove plug containing epoxy) when the forehead support is deformed to the desired position. The epoxy sets the forehead support in its desired position when it hardens or sets, e.g., via heat, predetermined time period, etc. Similar to the above arrangement, this provides a customized, fixable position for the forehead support.

5. Fifth Embodiment of Forehead Support

Figure 18:
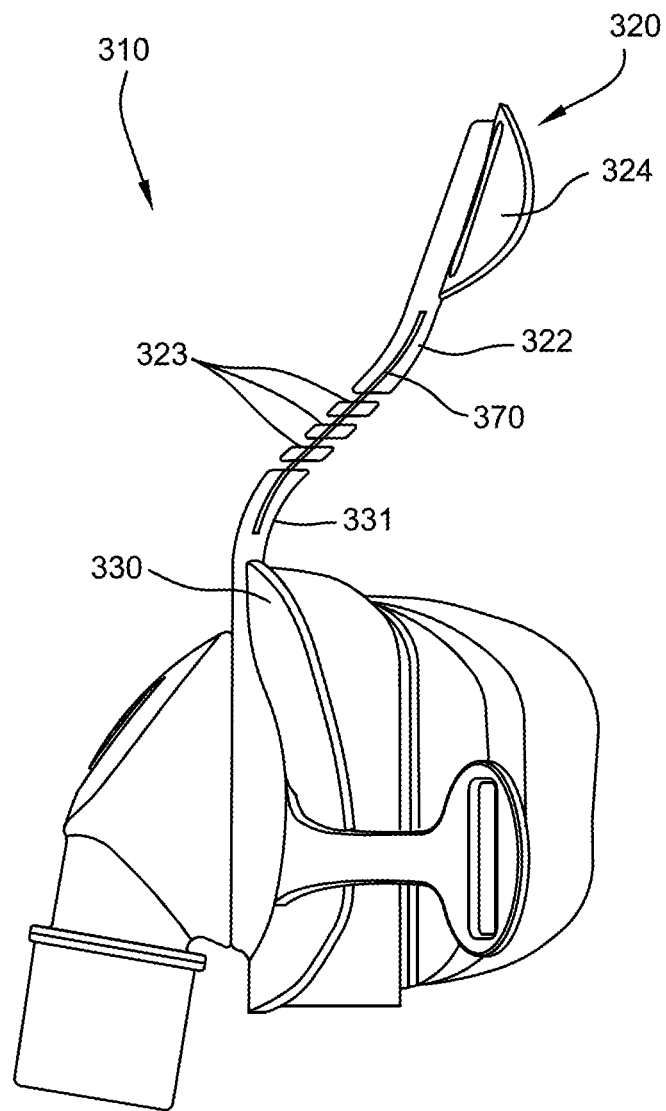
FIG. 18 is a side view of a mask including a forehead support with a malleable support member according to an embodiment of the present invention.

FIG. 18 illustrates a respiratory mask 310 including a forehead support 320 according to another embodiment of the present invention. In this embodiment, the forehead support 320 is manufactured from two or more materials and includes a stiff support structure 331 that is connected to the frame 330 plus a malleable support member 370 (e.g., such as a shape memory alloy, aluminum, magnesium/titanium alloy, or wire, e.g., nitinol wire) that is then attached to a cross portion 324 of the forehead support. The forehead support 320 can then be easily deformed by bending the malleable support member 370.

As illustrated, the malleable support member 370 may be a metal wire provided along the base 322 with cut-outs 323 provided in the base 322 to expose the malleable support member 370. The cut-outs 323 allow the malleable support member 370 to bend at points along the base 322, and the malleable support member 370 is structured to hold its desired position.

6. Sixth Embodiment of Forehead Support

Figure 19:
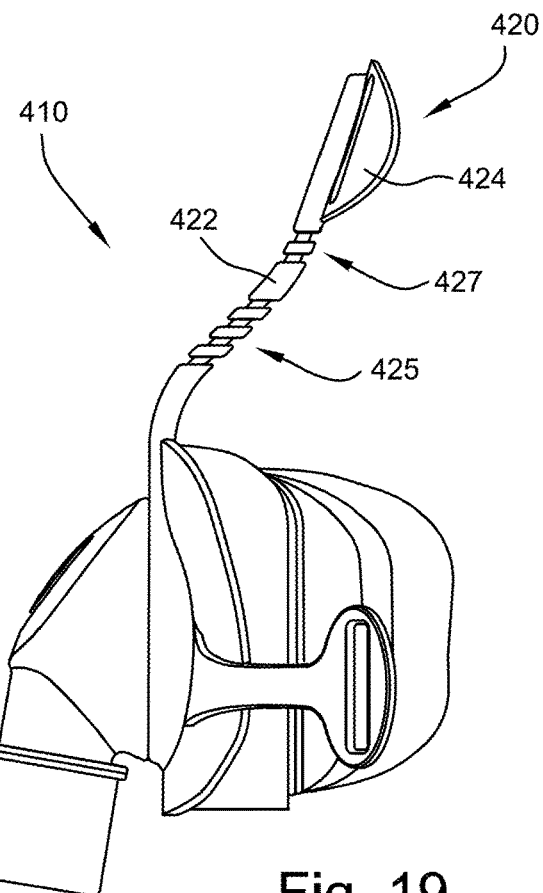
FIG. 19 is a side view of a mask including a forehead support with first and second flexible portions according to an embodiment of the present invention.

FIG. 19 illustrates a respiratory mask 410 including a forehead support 420 according to another embodiment of the present invention. In this embodiment, the forehead support 420 includes a second flexible portion 427 at the joint between the base 422 and the upper cross portion 424. The second flexible portion 427 may be provided by cut-outs (similar to the first flexible portion 425) or other suitable configurations, e.g., living hinge. This arrangement allows the upper cross portion 424 to flex in either direction (counter-rotating) with respect to the base 422 to maximize surface area contact with the patient's forehead, e.g., cross-arm parallel to the patient's forehead. That is, the counter-rotating second flexible portion 427 allows the forehead support 420 to accommodate extreme positions while avoiding edge contact.

It should be appreciated that the forehead support 420 may include flexible portions (e.g., cut-outs, living hinges, etc.) at other suitable locations where bending may be desired, e.g., along the cross-portion.

In this embodiment, the first and second flexible portions of the forehead support are resilient so that they substantially return to their original unloaded positions when not loaded, e.g., from headgear. Alternatively, the first and/or second flexible portions may be deformable (e.g., plastically deformable, malleable) so that they substantially retain their flexed or adjusted positions when not loaded.

7. Seventh Embodiment of Forehead Support

Figures 1, 20:
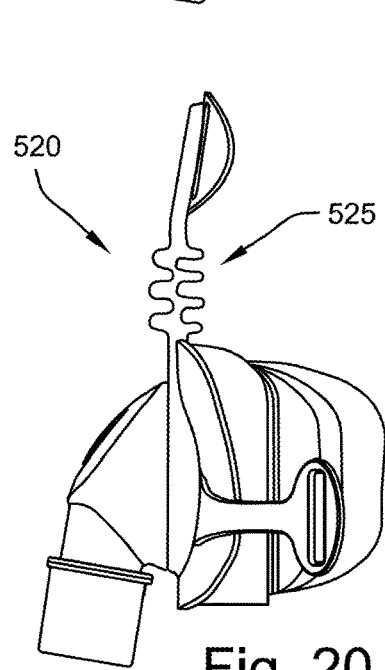
Figures 2, 20:
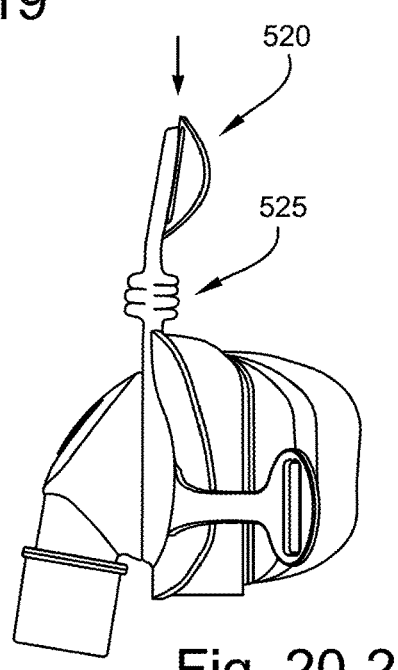

FIGS. 20-1 and 20-2 illustrate a respiratory mask including a forehead support 520 according to another embodiment of the present invention. In this embodiment, the forehead support 520 includes a flexible portion 525 along the base which allows the forehead support to flex across a useful angular range in any plane and to extend or compress axially in use. For example, FIG. 20-1 illustrates the forehead support in an unloaded position, and FIG. 20-2 illustrates the forehead support when loaded and compressed axially. As illustrated, the flexible portion has a wavy or general s-shape. However, other suitable arrangements are possible to allow axial compression, e.g., bellows type arrangement.

In an embodiment, the flexible portion may structured such that it is adapted to provide plastic compression or extension and elastic flexing or bending. For example, the flexible portion may be plastically extended or compressed to maintain the same height while adaptively bending across a useful angular range in use. In another embodiment, the flexible portion may provide plastic compression/extension and plastic bending.

Thus, the flexible portion of the forehead support may be structured to provide an angular and/or axial range of movement, and such movement may be varied using plastic and/or elastic materials.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:
1. A respiratory mask, comprising:
   a mask frame;
   a cushion provided to the mask frame and adapted to form a seal on at least a nasal bridge region of a patient's face;
   an elbow provided to the mask frame and adapted to connect to an air delivery tube that delivers breathable gas to the patient;
   headgear; and a forehead support provided to the mask frame, the forehead support including a base extending directly from the mask frame and a headgear connector provided to the base, wherein the forehead support is superior to the elbow, wherein the base includes a flexible portion along at least a portion of a length of the base including a material and/or physical characteristic that allows the forehead support to flex from an original, unloaded position to an equilibrium position to fit a patient's forehead, and wherein the flexible portion is structured to bias the headgear connector away from the patient's forehead such that the headgear connector is adapted to be spaced away from the patient's forehead in the original, unloaded position, and the headgear connector is adapted to be flexed towards the patient's forehead to the equilibrium position when headgear tension is applied.

2. A respiratory mask according to claim 1, wherein the flexible portion includes one or more recesses or cut-outs extending along at least a portion of the base.

3. A respiratory mask according to claim 2, wherein the one or more recesses or cut-outs extend transversely to a main axis of the mask frame.

4. A respiratory mask according to claim 2, wherein the one or more recesses or cut-outs extend about a perimeter of the base.

5. A respiratory mask according to claim 2, wherein the one or more recesses or cut-outs are structured to control an amount and location of flexing.

6. A respiratory mask according to claim 1, wherein the base includes a cross-section in a frontal plane that is thicker than a cross-section in a medial plane.

7. A respiratory mask according to claim 1, wherein at least the flexible portion is constructed of a resilient material that allows the forehead support to substantially return to its original, unloaded position when not loaded.

8. A respiratory mask according to claim 1, wherein the base is flexible in opposing directions from the original, unloaded position.

9. A respiratory mask according to claim 1, wherein the forehead support is structured to provide flexibility towards and away from the patient's face and to allow limited axial flex or rotation along a longitudinal axis of the base.

10. A respiratory mask according to claim 1, wherein the flexible portion allows auto-fitting of the mask.

11. A respiratory mask according to claim 1, wherein the mask frame and forehead support are integrally formed in one piece.

12. A respiratory mask according to claim 1, further comprising lower headgear connectors provided to respective sides of the mask frame, each of the lower headgear connectors being in the form of an outrigger including an elongated arm and a tab portion that provides a slot adapted to receive a respective lower headgear strap in use.

13. A respiratory mask according to claim 1, wherein the forehead support has a general "T"-shape with an upper cross-portion provided to the base.

14. A respiratory mask according to claim 13, wherein the upper cross-portion includes slots adapted to receive respective headgear straps in use.

15. A respiratory mask according to claim 13, wherein the upper cross-portion is structured to retain one or more forehead pads.

16. A respiratory mask according to claim 1, wherein the base includes a spring constant.

17. A respiratory mask according to claim 1, wherein the forehead support has a general "T"-shape with an upper cross-portion provided to the base, and the flexible portion is provided as a distinct structure positioned entirely between the upper cross-portion and the frame.

18. A respiratory mask according to claim 1, wherein the flexible portion provides a distinct location of flexion of the base.

19. A respiratory mask according to claim 1, wherein the forehead support is adapted to be flexed inwardly towards the patient's forehead to fit the patient's forehead.

20. A respiratory mask according to claim 1, wherein the headgear connector is oriented at an angle with respect to the base in the unloaded position.

21. A respiratory mask according to claim 1, wherein the headgear connector includes an upper cross-portion provided to the base, the upper cross-portion including slots adapted to receive respective headgear straps of the headgear.

22. A respiratory mask according to claim 1, wherein the base includes a non-linear configuration along its length in the unloaded position.

23. A respiratory mask according to claim 1, wherein the headgear connector is oriented at an angle in the unloaded position, and the angle extends in an anterior-superior direction relative to a frontal plane of the patient.

24. A respiratory mask according to claim 1, wherein the headgear connector is oriented at an angle in the unloaded position, and the angle extends in an anterior-superior direction relative to a vertical plane of the mask frame.

25. A respiratory mask according to claim 24, wherein at least a portion of the base is oriented at an angle relative to the vertical plane of the mask frame in the unloaded position.

26. A respiratory mask according to claim 1, wherein the frame includes a tube portion structured to retain the elbow.

27. A respiratory mask according to claim 1, wherein the elbow includes a vent arrangement for gas washout.

28. A respiratory mask according to claim 1, wherein the elbow includes a first portion structured to interface or otherwise attach to the frame and a second portion provided to a swivel joint adapted to connect to the air delivery tube.

29. A respiratory mask according to claim 1, wherein the cushion is provided to a rear of the frame, the elbow is provided to a front of the frame, and the forehead support is a direct extension from a top of the frame.

* * * * *